United States Patent
Song et al.

(10) Patent No.: US 10,345,706 B2
(45) Date of Patent: *Jul. 9, 2019

(54) MONOMER FOR HARDMASK COMPOSITION AND HARDMASK COMPOSITION INCLUDING THE MONOMER AND METHOD OF FORMING PATTERNS USING THE HARDMASK COMPOSITION

(71) Applicants: Hyun-Ji Song, Uiwang-si (KR); Yun-Jun Kim, Uiwang-si (KR); Go-Un Kim, Uiwang-si (KR); Young-Min Kim, Uiwang-si (KR); Hea-Jung Kim, Uiwang-si (KR); Joon-Young Moon, Uiwang-si (KR); Yo-Choul Park, Uiwang-si (KR); Yu-Shin Park, Uiwang-si (KR); You-Jung Park, Uiwang-si (KR); Seung-Wook Shin, Uiwang-si (KR); Yong-Woon Yoon, Uiwang-si (KR); Chung-Heon Lee, Uiwang-si (KR); Yoo-Jeong Choi, Uiwang-si (KR); Seung-Hee Hong, Uiwang-si (KR)

(72) Inventors: Hyun-Ji Song, Uiwang-si (KR); Yun-Jun Kim, Uiwang-si (KR); Go-Un Kim, Uiwang-si (KR); Young-Min Kim, Uiwang-si (KR); Hea-Jung Kim, Uiwang-si (KR); Joon-Young Moon, Uiwang-si (KR); Yo-Choul Park, Uiwang-si (KR); Yu-Shin Park, Uiwang-si (KR); You-Jung Park, Uiwang-si (KR); Seung-Wook Shin, Uiwang-si (KR); Yong-Woon Yoon, Uiwang-si (KR); Chung-Heon Lee, Uiwang-si (KR); Yoo-Jeong Choi, Uiwang-si (KR); Seung-Hee Hong, Uiwang-si (KR)

(73) Assignee: CHEIL INDUSTRIES, INC., Gumi-si, Gyeongsangbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/258,489

(22) Filed: Apr. 22, 2014

(65) Prior Publication Data
US 2015/0001178 A1    Jan. 1, 2015

(30) Foreign Application Priority Data

Jun. 26, 2013  (KR) .................. 10-2013-0073947
Jun. 26, 2013  (KR) .................. 10-2013-0073948
Jun. 26, 2013  (KR) .................. 10-2013-0073949

(51) Int. Cl.
| G03F 7/40 | (2006.01) |
| G03F 7/38 | (2006.01) |
| G03F 7/36 | (2006.01) |
| G03F 7/30 | (2006.01) |
| G03F 7/09 | (2006.01) |
| G03F 7/11 | (2006.01) |
| C07C 39/12 | (2006.01) |
| C07C 323/19 | (2006.01) |
| C07C 217/58 | (2006.01) |

(Continued)

(52) U.S. Cl.
CPC ............... $G03F\ 7/40$ (2013.01); $C07C\ 22/04$ (2013.01); $C07C\ 39/12$ (2013.01); $C07C\ 39/225$ (2013.01); $C07C\ 217/58$ (2013.01); $C07C\ 255/53$ (2013.01); $C07C\ 323/19$ (2013.01); $C07D\ 215/14$ (2013.01); $C07D\ 311/58$ (2013.01); $C07D\ 333/16$ (2013.01); $C07D\ 333/50$ (2013.01); $G03F\ 7/09$ (2013.01); $G03F\ 7/091$ (2013.01); $G03F\ 7/094$ (2013.01); $G03F\ 7/11$ (2013.01); $G03F\ 7/30$ (2013.01); $G03F\ 7/36$ (2013.01); $G03F\ 7/38$ (2013.01); $C07C\ 2601/14$ (2017.05); $C07C\ 2603/50$ (2017.05); $C07C\ 2603/52$ (2017.05); $C07C\ 2603/54$ (2017.05)

(58) Field of Classification Search
None
See application file for complete search history.

(56) References Cited

U.S. PATENT DOCUMENTS 7,862,990 B2    1/2011  Yoon et al.
8,637,219 B2 *  1/2014  Cho .................... C07C 33/26
                                          430/270.1

(Continued)

FOREIGN PATENT DOCUMENTS

CN    101641390 A    2/2010
CN    102115426 A    7/2011

(Continued)

OTHER PUBLICATIONS

Machine-assisted English translation for KR 10-2013-0078745 (2013).*

(Continued)

*Primary Examiner* — Sin J Lee
(74) *Attorney, Agent, or Firm* — Lee & Morse, P.C.

(57) ABSTRACT

A monomer for a hardmask composition is represented by the following Chemical Formula 1,

[Chemical Formula 1]

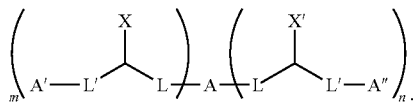

10 Claims, 1 Drawing Sheet

(51) Int. Cl.
*C07C 22/04* (2006.01)
*C07C 255/53* (2006.01)
*C07C 39/225* (2006.01)
*C07D 215/14* (2006.01)
*C07D 333/16* (2006.01)
*C07D 333/50* (2006.01)
*C07D 311/58* (2006.01)

(56) References Cited

U.S. PATENT DOCUMENTS

| | | | | |
|---|---|---|---|---|
| 8,952,373 | B2 * | 2/2015 | Choi et al. | 257/40 |
| 9,018,776 | B2 * | 4/2015 | Song | H01L 21/02118 106/287.26 |
| 9,158,201 | B2 * | 10/2015 | Lee | G03F 7/26 |
| 9,359,276 | B2 * | 6/2016 | Choi | C07C 39/14 |
| 9,513,546 | B2 * | 12/2016 | Park | C07C 49/792 |
| 9,529,257 | B2 * | 12/2016 | Lee | G03F 7/094 |
| 9,556,094 | B2 * | 1/2017 | Kim | C07C 39/14 |
| 10,066,057 | B2 * | 9/2018 | Park | C08G 73/0672 |
| 2003/0194647 | A1 * | 10/2003 | Huang | G03F 7/11 430/271.1 |
| 2009/0082576 | A1 * | 3/2009 | Lindsey | C07D 207/34 548/402 |
| 2009/0273100 | A1 * | 11/2009 | Aton et al. | 257/786 |
| 2010/0021830 | A1 * | 1/2010 | Kim et al. | 430/5 |
| 2010/0102373 | A1 * | 4/2010 | Li et al. | 257/301 |
| 2010/0316949 | A1 | 12/2010 | Rahman et al. | |
| 2011/0155944 | A1 * | 6/2011 | Cho et al. | 252/62.51 R |
| 2012/0153511 | A1 * | 6/2012 | Song | H01L 21/02118 257/786 |
| 2014/0183701 | A1 * | 7/2014 | Choi et al. | 257/618 |
| 2014/0342273 | A1 * | 11/2014 | Kim | G03F 7/094 430/5 |
| 2015/0008212 | A1 * | 1/2015 | Choi | C07C 39/14 216/41 |
| 2015/0205198 | A1 * | 7/2015 | Lee | G03F 7/094 216/49 |
| 2015/0301448 | A1 * | 10/2015 | Park | C07C 49/792 216/49 |
| 2017/0327640 | A1 * | 11/2017 | Kim | H01L 21/02282 |

FOREIGN PATENT DOCUMENTS

| | | |
|---|---|---|
| CN | 102540729 A | 7/2012 |
| CN | 102566281 A | 7/2012 |
| CN | 102566282 A | 7/2012 |
| CN | 103903962 A | 7/2014 |
| JP | 62-252734 A | 11/1987 |
| JP | 06-219973 A | 8/1994 |
| JP | 2001-098358 A | 4/2001 |
| JP | 2004-158709 A | 6/2004 |
| JP | 2012-001687 A | 1/2012 |
| KR | 10-0796047 B1 | 1/2008 |
| KR | 10-2010-0023868 A | 3/2010 |
| KR | 2011-0043652 A | 4/2011 |
| KR | 10-2011-0053136 A | 5/2011 |
| KR | 10-2011-0079201 A | 7/2011 |
| KR | 2011-0084900 A | 7/2011 |
| KR | 2011-0084901 A | 7/2011 |
| KR | 2011-0118781 A | 11/2011 |
| KR | 10-2012-0067602 A | 6/2012 |
| KR | 10-2012-0068379 A | 6/2012 |
| KR | 10-2012-0073817 A | 7/2012 |
| KR | 2012-0102646 A | 9/2012 |
| KR | 10-2013-0003059 A | 1/2013 |
| KR | 10-2013-0078432 A | 7/2013 |
| KR | 10-2013-0078745 A | 7/2013 |
| KR | 10-2014-0085124 A | 7/2014 |
| KR | 10-2015-0002929 A | 1/2015 |
| TW | 201134799 A | 10/2011 |
| WO | WO 2013/100409 A1 * | 7/2013 |

OTHER PUBLICATIONS

Kumar et al ("Condensation of propargylic alcohols with N-methylcarbazole and carbazole in [bmim]PF6 ionic liquid; synthesis of novel dipropargylic carbazoles using TfOH or Bi(NO3)3. 5H2O as catalyst", Tetrahedron Letters, vol. 54 (2013), p. 965-969). (Year: 2013).*

Vigmond et al (Chemical Abstract (Accession No. 1994:435241) for "Direct synthesis of aryldipyrromethanes", Tetrahedron Letters (1994), vol. 35(16), p. 2455-8). (Year: 1994).*

Dogutan et al ("Investigation of the Scope of a New Route to ABCD-Bilanes and ABCD-Porphyrins", Journal of Organic Chemistry (2008), vol.73(17), p. 6728-6742). (Year: 2008).*

Koszarna et al ("Efficient Synthesis of meso-Substituted Corroles in a H2O-MeOH Mixture", Journal of Organic Chemistry (2006), 71(10), p. 3707-3717). (Year: 2006).*

Cottone et al ("Synthesis and Reactivity of Bi-, Tri-, and Tetrametallic Aluminum Tetraphenolate Complexes", Organometallics 2002), vol. 21, p. 3610-3627). (Year: 2002).*

Machine-assisted English translation for KR 10-2012-0068379 (Choi et al). (Year: 2012).*

Manirul Islam, et al.; "Highly efficient recyclable heterogeneous palladium catalyst for C—C coupling, amination and cyanation reactions"; Journal of Organometallic Chemistry 695, (2010), 2284-2295.

Daniel R. Zuidema, et al.; (2011) "Deoxygenation of Aromatic Ketones Using Transfer Hydrogenolysis with Raney Nickel in 2-Propanol"; Synthetic Communications, 41:19,: 2927-2931, 2011.

Norman L. Holy; "Versatile Polymer-Bound Hydrogenation Catalysts. Rhodium (I)-Catalyzed Hydrogenation"; J. Org. Chem., vol. 44, No. 2, 1970; 239-243.

Taiwanese Search Report dated Sep. 18, 2015 in Corresponding Taiwanese Patent Application No. 103103336.

Chinese Search Report dated Feb. 23, 2016 for corresponding Chinese Patent Application No. 201410163675.8, Song, et al.

Provisional double patenting rejection over claims of the above-identifed application; USPTO Office action dated Mar. 30, 2016, in U.S. Appl. No. 14/364,829.

* cited by examiner

[Calculation Equation 2]
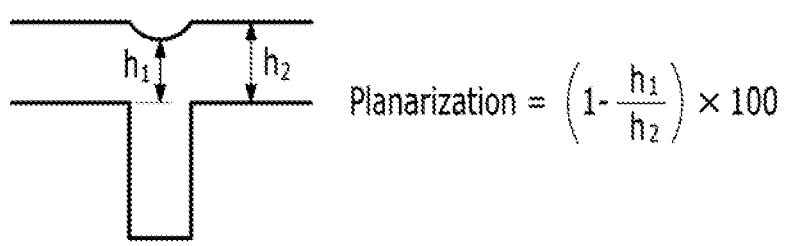

MONOMER FOR HARDMASK COMPOSITION AND HARDMASK COMPOSITION INCLUDING THE MONOMER AND METHOD OF FORMING PATTERNS USING THE HARDMASK COMPOSITION

CROSS-REFERENCE TO RELATED APPLICATION

Korean Patent Application Nos. 10-2013-0073947, 10-2013-0073948, and 10-2013-0073949, each filed on Jun. 26, 2013, in the Korean Intellectual Property Office, and entitled: "Monomer for Hardmask Composition and Hardmask Composition including the Monomer and Method of Forming Patterns using the Hardmask Composition," are incorporated by reference herein in their entirety.

BACKGROUND

1. Field

Embodiments relate to a monomer for a hardmask composition, a hardmask composition including the monomer and a method of forming patterns using the hardmask composition.

2. Description of the Related Art

Recently, the semiconductor industry has developed to an ultra-fine technique having a pattern of several to several tens nanometer size. Such ultrafine technique essentially needs effective lithographic techniques.

SUMMARY

Embodiments are directed to a monomer for a hardmask composition, the monomer being represented by the following Chemical Formula 1,

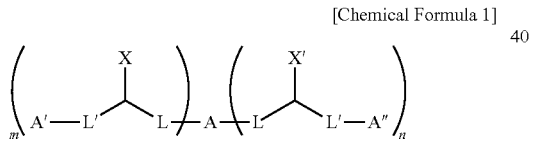

[Chemical Formula 1]

In the above Chemical Formula 1,

A may be a substituted or unsubstituted C1 to C20 alkylene group, a substituted or unsubstituted C2 to C20 alkenylene group, a substituted or unsubstituted C2 to C20 alkynylene group, or a substituted or unsubstituted cyclic group, A' and A" may independently be a substituted or unsubstituted cyclic group, X and X' may independently be a hydroxy group, a halogen atom, a halogen-containing group, a thionyl group, a thiol group, a cyano group, a substituted or unsubstituted amino group, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C30 alkoxy group, a substituted or unsubstituted C2 to C30 alkenyl group, a substituted or unsubstituted C2 to C30 alkynyl group, a substituted or unsubstituted C1 to C20 aldehyde group, a substituted or unsubstituted C1 to C4 alkyl ether, a substituted or unsubstituted C7 to C20 arylalkylene ether, a substituted or unsubstituted C1 to C30 haloalkyl group, a substituted or unsubstituted C1 to C20 alkylborane group, a substituted or unsubstituted C6 to C30 arylborane group, or a combination thereof, L and L' may independently be a single bond, a substituted or unsubstituted C1 to C20 alkylene group, a substituted or unsubstituted C6 to C30 arylene group, or a combination thereof, and m and n may independently be integers of greater than or equal to 0, and 1≤m+n≤(a maximum number of a substituent of A), wherein, at least one of A' and A" is a substituted cyclic group, in the case A' and A" do not include any hetero atoms.

At least one of the A, A', or A" may be a substituted or unsubstituted cyclic group selected from the following Groups 1 to 3.

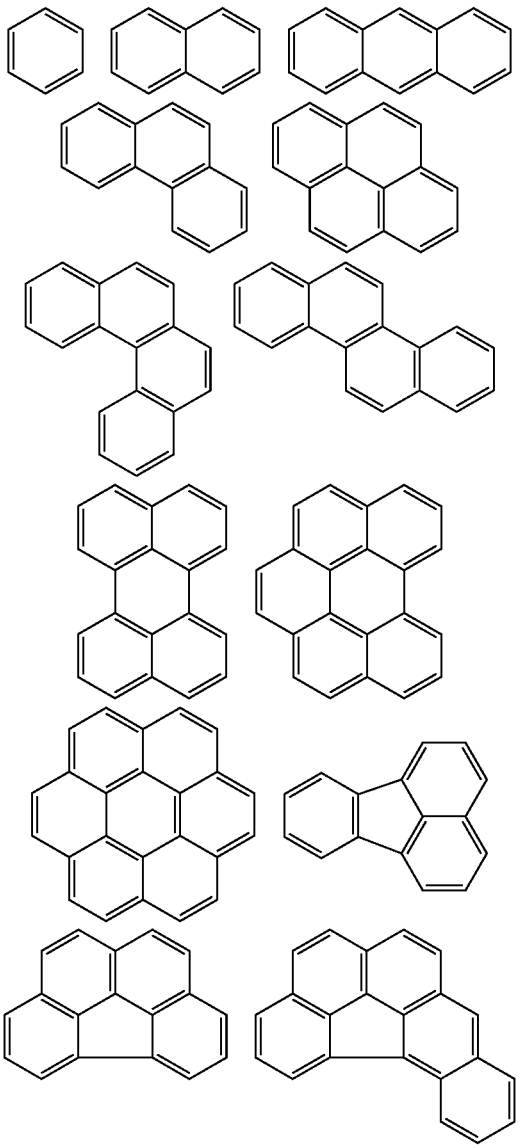

[Group 1]

-continued

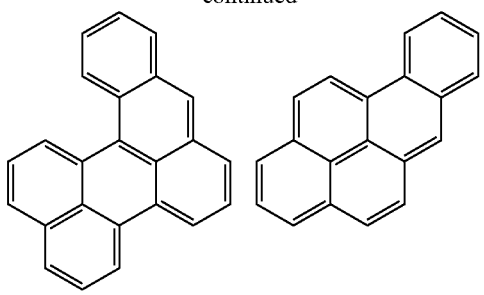

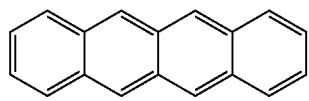

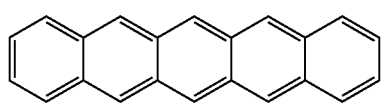

-continued

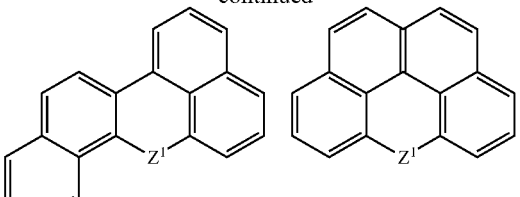

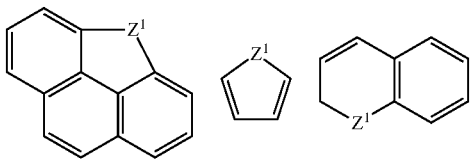

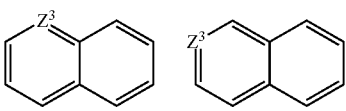

[Group 2]

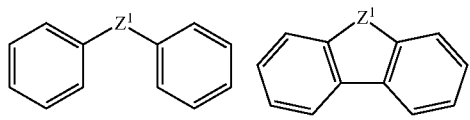

[Group 3]

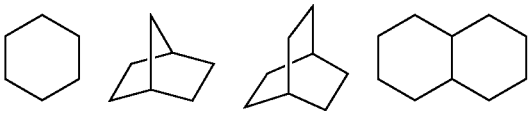

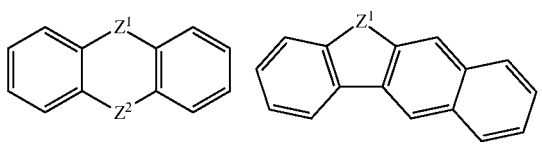

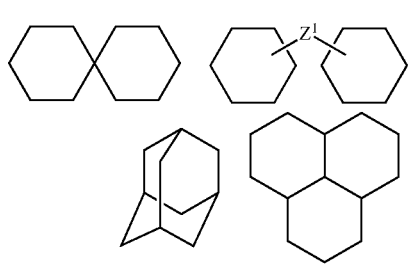

In the Groups 2 and 3, $Z^1$ and $Z^2$ may independently be a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, $Z^3$ may be nitrogen (N), CR, or a combination thereof, and R may be hydrogen, a substituted or unsubstituted C1 to C10 alkyl group, a halogen atom, a halogen-containing group, or a combination thereof.

At least one of the A, A', or A" may be a substituted or unsubstituted polycyclic aromatic group.

At least one hydrogen of the A, A', or A" may be substituted with a hydroxy group, a thionyl group, a thiol group, a cyano group, a substituted or unsubstituted amino group, a halogen atom, a halogen-containing group, a substituted or unsubstituted C1 to C30 alkoxy group, or a combination thereof.

The monomer may be represented by one selected from the following Chemical Formulae 1a to 1o.

[Chemical Formula 1a]
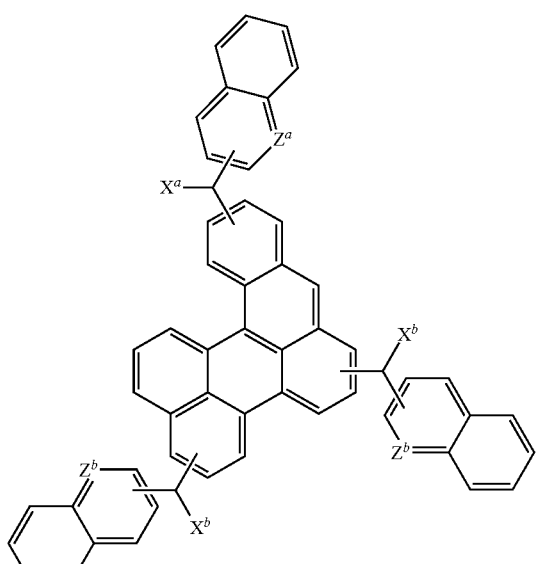
[Chemical Formula 1b]
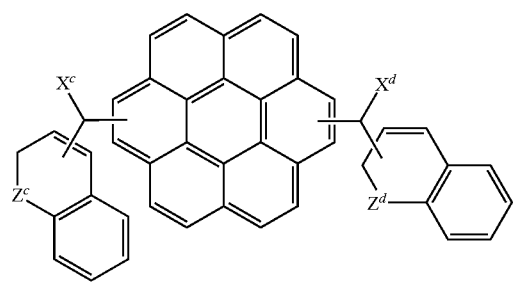
[Chemical Formula 1c]
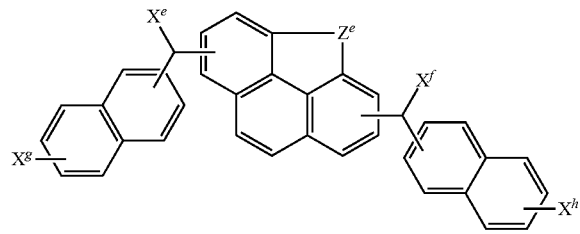
[Chemical Formula 1d]
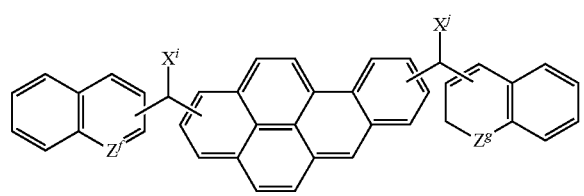
[Chemical Formula 1e]
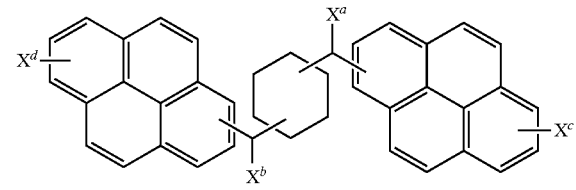
[Chemical Formula 1f]
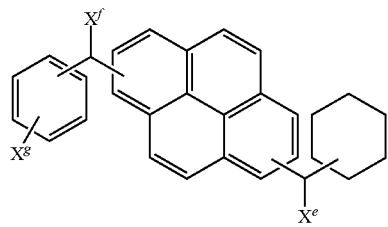
[Chemical Formula 1g]
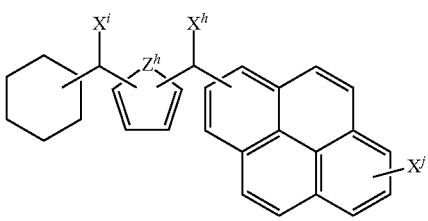
[Chemical Formula 1h]
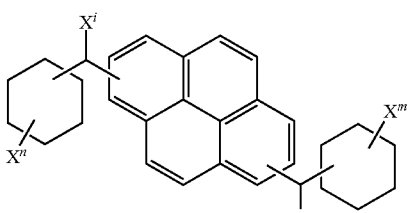
[Chemical Formula 1i]
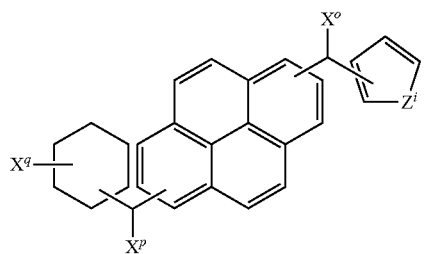
[Chemical Formula 1j]
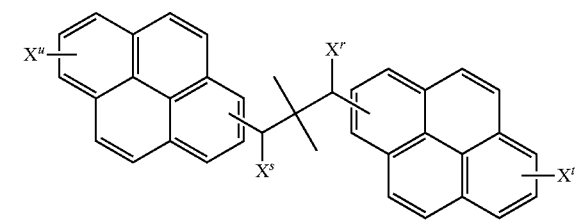
[Chemical Formula 1k]
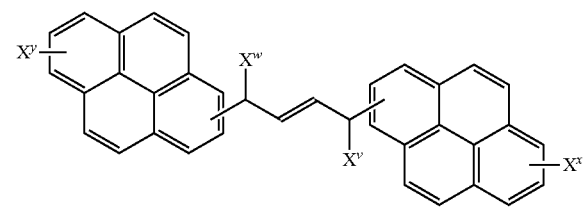

-continued

[Chemical Formula 1l]

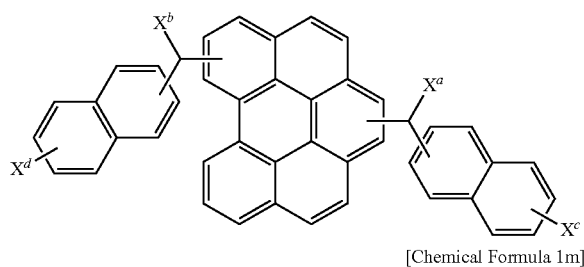

[Chemical Formula 1m]

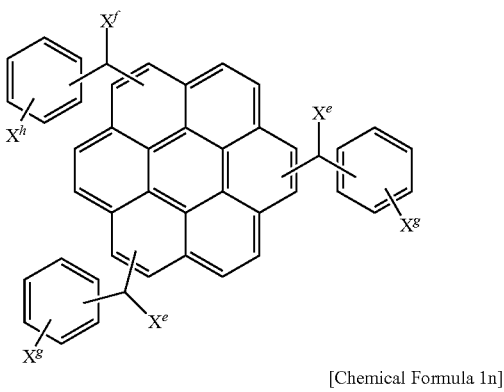

[Chemical Formula 1n]

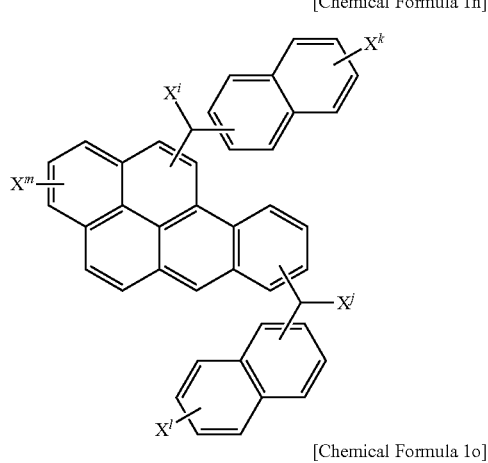

[Chemical Formula 1o]

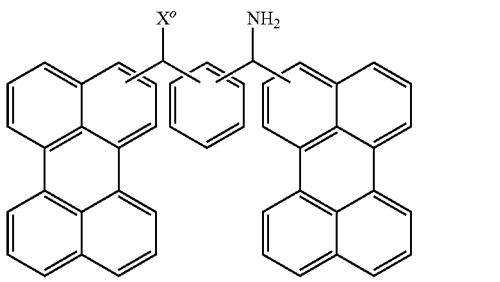

In the above Chemical Formulae 1a to 1o, $X^a$ to $X^y$ may independently be a hydroxy group, a halogen atom, a halogen-containing group, a thionyl group, a thiol group, a cyano group, a substituted or unsubstituted amino group, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C30 alkoxy group, a substituted or unsubstituted C2 to C30 alkenyl group, a substituted or unsubstituted C2 to C30 alkynyl group, a substituted or unsubstituted C1 to C20 aldehyde group, a substituted or unsubstituted C1 to C4 alkyl ether, a substituted or unsubstituted C7 to C20 arylalkylene ether, a substituted or unsubstituted C1 to C30 haloalkyl group, a substituted or unsubstituted C1 to C20 alkylborane group, a substituted or unsubstituted C6 to C30 arylborane group, or a combination thereof, $Z^c$, $Z^d$, $Z^e$, $Z^g$, $Z^h$, and $Z^i$ may independently be a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, $Z^a$, $Z^b$, and $Z^f$ may independently be nitrogen (N), CR, or a combination thereof, and R may be hydrogen, a substituted or unsubstituted C1 to C10 alkyl group, a halogen atom, a halogen-containing group, or a combination thereof.

The monomer may have a molecular weight of about 200 to about 5,000.

Embodiments are also directed to a hardmask composition including the monomer represented by the above Chemical Formula 1 and a solvent.

The monomer may be included in an amount of about 0.1 wt % to about 50 wt % based on the total amount of the hardmask composition.

Embodiments are also directed to a method of forming a pattern, the method including providing a material layer on a substrate, applying a hardmask composition according to an embodiment on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The hardmask composition may be applied using a spin-on coating method.

Forming the hardmask layer may include heat-treating at about 100° C. to about 500° C.

The method may further include forming a bottom anti-reflective coating (BARC) on the silicon-containing thin layer.

The silicon-containing thin layer may include silicon oxynitride (SiON).

BRIEF DESCRIPTION OF THE DRAWINGS

Features will become apparent to those of skill in the art by describing in detail example embodiments with reference to the attached drawings in which:

FIG. 1 illustrates Calculation Equation 2.

DETAILED DESCRIPTION

Example embodiments will now be described more fully hereinafter; however, they may be embodied in different forms and should not be construed as limited to the embodiments set forth herein. Rather, these embodiments are provided so that this disclosure will be thorough and complete, and will fully convey exemplary implementations to those skilled in the art.

As used herein, when a definition is not otherwise provided, the term 'substituted' may refer to one substituted with a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a substituted or unsubstituted C1 to C20 alkylborane group, a substituted or unsubstituted C6 to C30 arylborane group, a C1 to C4 alkoxy group, a C1 to C20 heteroalkyl group, a C3 to C20 heteroarylalkyl group, C3 to C30 cycloalkyl group, a C3 to C15 cycloalkenyl group, a C6 to C15 cycloalkynyl group, C2 to C30 heterocycloalkyl group, and a combination thereof, instead of a hydrogen atom of a compound.

As used herein, when a definition is not otherwise provided, the term 'hetero' refers to one including 1 to 3 heteroatoms selected from B, N, O, S, and P.

Hereinafter, a monomer for a hardmask composition according to an example embodiment is described.

The monomer for a hardmask composition according to an example embodiment may be represented by the following Chemical Formula 1.

[Chemical Formula 1]

$$\left( A'-L'\overset{X}{\underset{}{\bigwedge}} \right)_m \left( L-A-L'\overset{X'}{\underset{}{\bigwedge}} L'-A'' \right)_n$$

According to the present example embodiment, in the above Chemical Formula 1,

A is a substituted or unsubstituted C1 to C20 alkylene group, a substituted or unsubstituted C2 to C20 alkenylene group, a substituted or unsubstituted C2 to C20 alkynylene group, or a substituted or unsubstituted cyclic group, A' and A" are independently a substituted or unsubstituted cyclic group, X and X' are independently a hydroxy group, a halogen atom, a halogen-containing group, a thionyl group, a thiol group, a cyano group, a substituted or unsubstituted amino group, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C30 alkoxy group, a substituted or unsubstituted C2 to C30 alkenyl group, a substituted or unsubstituted C2 to C30 alkynyl group, a substituted or unsubstituted C1 to C20 aldehyde group, a substituted or unsubstituted C1 to C4 alkyl ether, a substituted or unsubstituted C7 to C20 arylalkylene ether, a substituted or unsubstituted C1 to C30 haloalkyl group, a substituted or unsubstituted C1 to C20 alkylborane group, a substituted or unsubstituted C6 to C30 arylborane group, or a combination thereof, L and L' are independently a single bond, a substituted or unsubstituted C1 to C20 alkylene group, a substituted or unsubstituted C6 to C30 arylene group, or a combination thereof, and m and n are independently integers of greater than or equal to 0, and 1≤m+n≤(a maximum number of a substituent of A), wherein, at least one of A' and A" is a substituted cyclic group, in the case A' and A" do not include any hetero atoms.

According to an example embodiment, at least one of the A, A', or A" is a substituted or unsubstituted cyclic group selected from the following Groups 1 to 3.

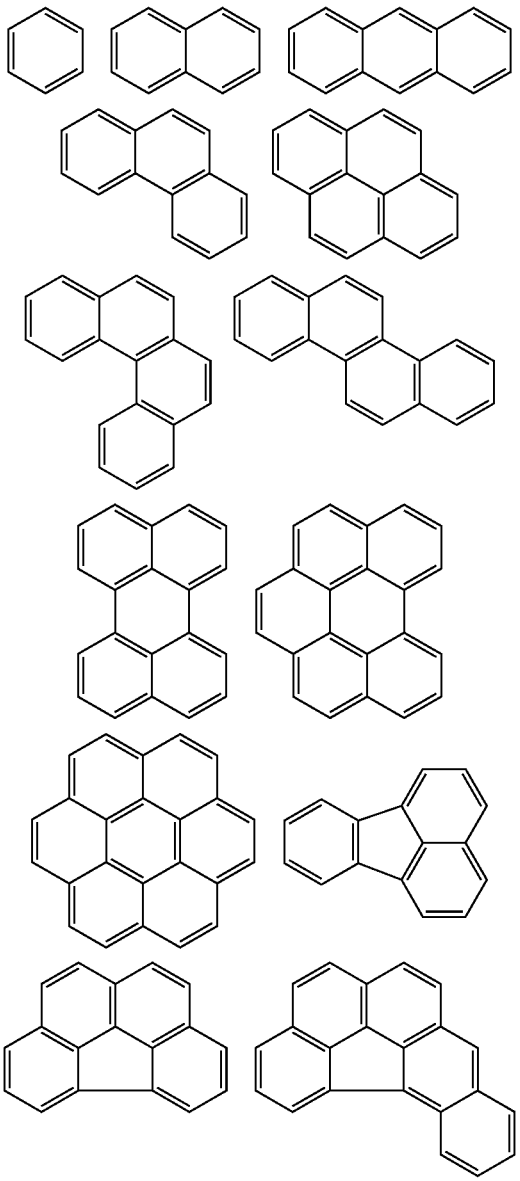

[Group 1]

-continued

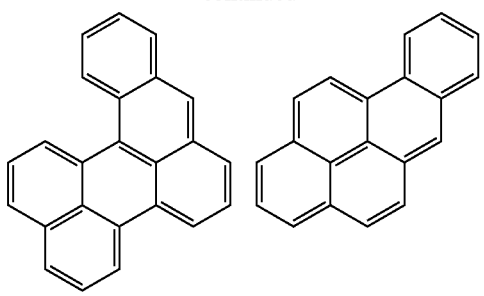
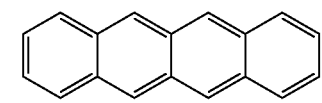
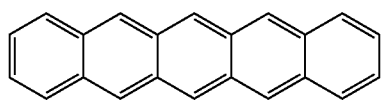

[Group 2]

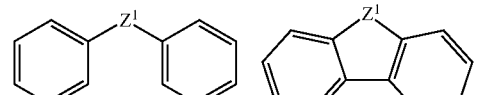
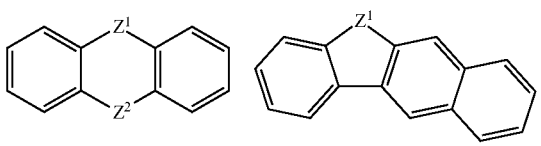
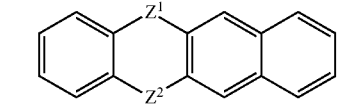
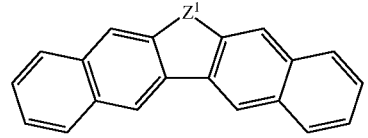
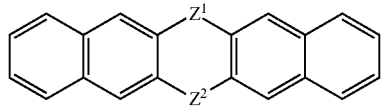
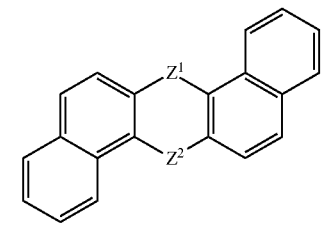
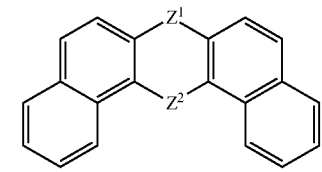

-continued

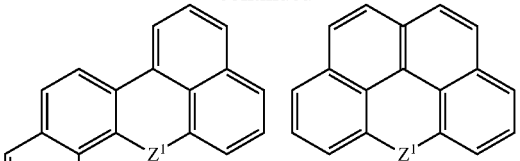
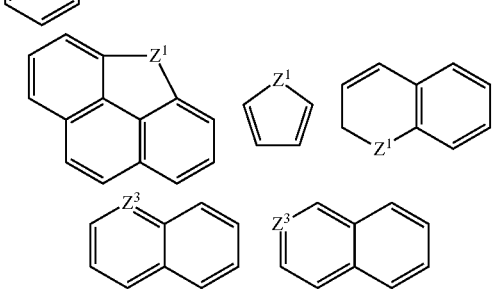

[Group 3]

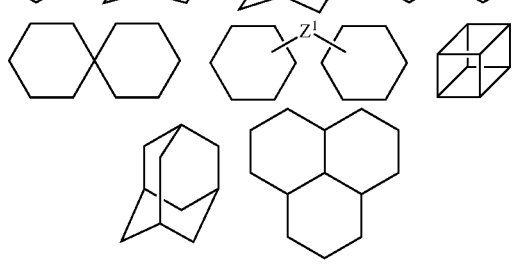

According to the present example embodiment, in the Groups 2 and 3, $Z^1$ and $Z^2$ are independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, $Z^3$ is nitrogen (N), CR, or a combination thereof, and R is hydrogen, a substituted or unsubstituted C1 to C10 alkyl group, a halogen atom, a halogen-containing group, or a combination thereof.

In the Groups 1 to 3, binding positions of each ring may be varied, and each ring may be substituted or unsubstituted. When the rings listed in the Group 1 are substituted rings, they may be substituted with, for example, a C1 to C20 alkyl group, a halogen atom, a hydroxy group, etc.

Various combinations the A, A', and A" may be provided.

For example, the A, A', and A" may be independently a substituted or unsubstituted aromatic group selected from the Groups 1 and 2.

For example, the A, A', and A" may independently be a substituted or unsubstituted aromatic group selected from the Groups 1 and 2, and at least one of A, A', and A" may be a group selected from the Group 2. When the monomer has a structure including at least one heteroaromatic ring group, affinity between the hardmask layer and a wafer layer may increase to improve gap-fill characteristics while helping to ensure etch resistance.

For example, the A may be a substituted or unsubstituted C1 to C20 alkylene group, a substituted or unsubstituted C2 to C20 alkenylene group, or a substituted or unsubstituted C2 to C20 alkynylene group, and the A' and A" may be one selected from the Groups 1 to 3.

For example, the A, A', and A" may independently be selected from the Groups 1 to 3, and at least one of the A, A', and A" may be selected from the Group 2 or Group 3.

According to the present example embodiment, in the above Chemical Formula 1, m and n indicating the number of a substituent are independently an integer of greater than or equal to about 0, and the m and n may be selected so that the sum of the m and n may not exceed a maximum number of a substituent of A.

According to the present example embodiment, the monomer includes a predetermined functional group (X and X') in the substituents, respectively. The monomer including these functional groups may exhibit improved solubility and may effectively form a hardmask layer in a spin-on coating method. In addition, when the spin-on coating method is used to form the hardmask layer on a lower layer having a predetermined pattern, gap-fill characteristics to fill a gap among patterns and planarization characteristics of the hardmask layer may be enhanced.

In addition, cross-linking may be amplified based on a condensation reaction of the functional groups, and excellent cross-linking characteristics may be provided. Accordingly, the monomer may be cross-linked into a polymer having a high molecular weight in a short time when heat-treated at a relatively low temperature and may show excellent characteristics for a hardmask layer such as mechanical characteristics, heat resistance properties, and etch resistance.

For example, at least one of the A, A', and A" may be a substituted or unsubstituted polycyclic aromatic group. In this way, when at least one of the polycyclic aromatic group is included, etch resistance may be improved.

For example, in the above Chemical Formula 1, at least one hydrogen of A, A', or A" may be substituted with a hydroxy group, a thionyl group, a thiol group, a cyano group, a substituted or unsubstituted amino group, halogen atom, a halogen-containing group, a substituted or unsubstituted C1 to C30 alkoxy group, or a combination thereof.

According to an example embodiment, the monomer may be represented by, for example, one of the following Chemical Formulae 1a to 1o.

[Chemical Formula 1a]

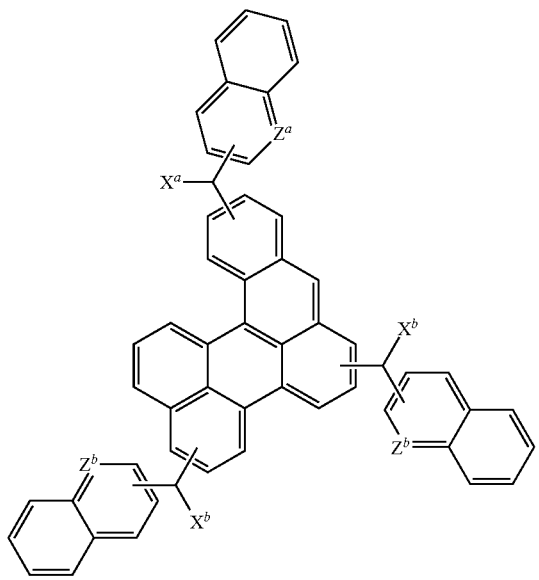

[Chemical Formula 1b]

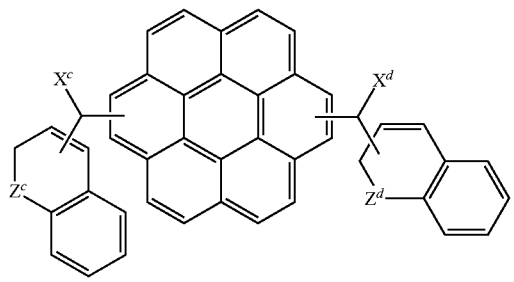

[Chemical Formula 1c]

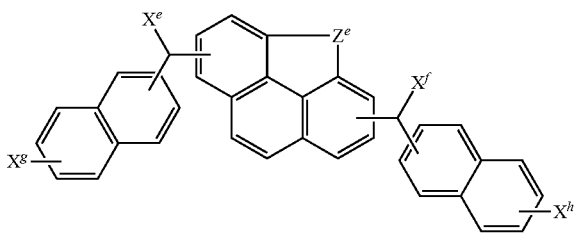

[Chemical Formula 1d]

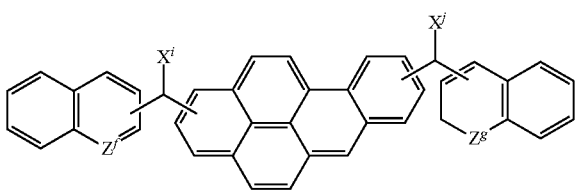

[Chemical Formula 1e]

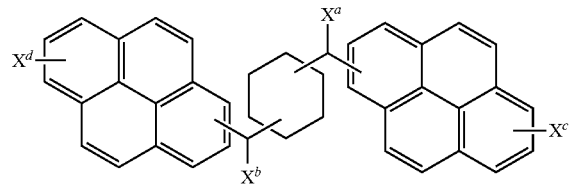

[Chemical Formula 1f]

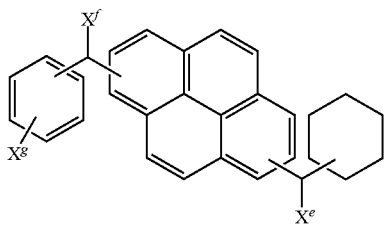

[Chemical Formula 1g]

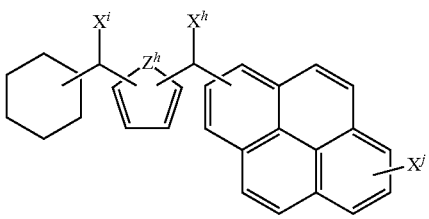

-continued

[Chemical Formula 1h]

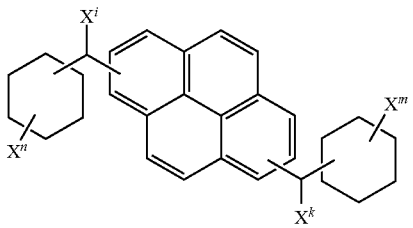

[Chemical Formula 1i]

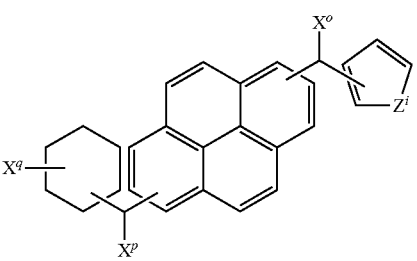

[Chemical Formula 1j]

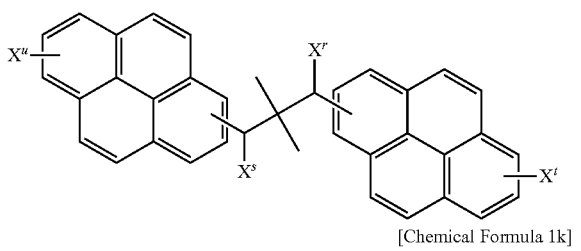

[Chemical Formula 1k]

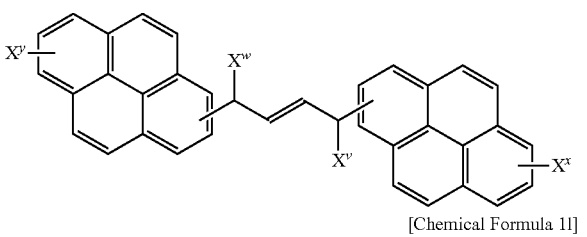

[Chemical Formula 1l]

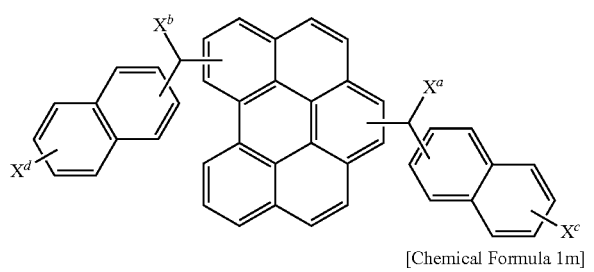

[Chemical Formula 1m]

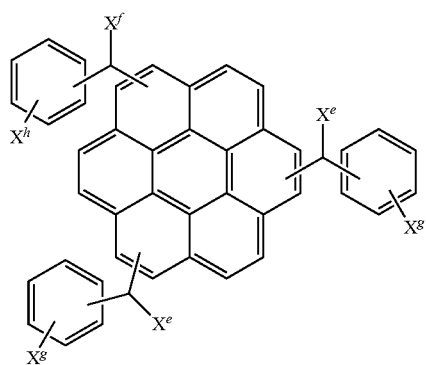

[Chemical Formula 1n]

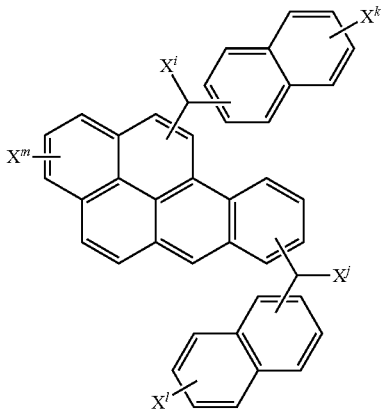

[Chemical Formula 1o]

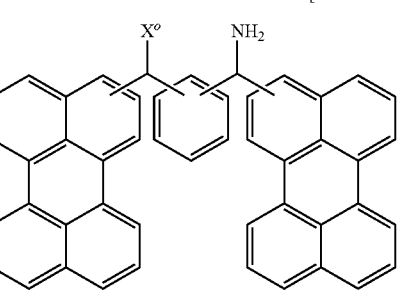

According to the present example embodiment, in the above Chemical Formulae 1a to 1o, X to X' are independently a hydroxy group, a halogen atom, a halogen-containing group, a thionyl group, a thiol group, a cyano group, a substituted or unsubstituted amino group, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C30 alkoxy group, a substituted or unsubstituted C2 to C30 alkenyl group, a substituted or unsubstituted C2 to C30 alkynyl group, a substituted or unsubstituted C1 to C20 aldehyde group, a substituted or unsubstituted C1 to C4 alkyl ether, a substituted or unsubstituted C7 to C20 arylalkylene ether, a substituted or unsubstituted C1 to C30 haloalkyl group, a substituted or unsubstituted C1 to C20 alkylborane group, a substituted or unsubstituted C6 to C30 arylborane group, or a combination thereof, $Z^c$, $Z^d$, $Z^e$, $Z^g$, $Z^h$, and $Z^i$ are independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, $Z^a$, $Z^b$, and $Z^f$ are independently nitrogen (N), CR, or a combination thereof, and R is hydrogen, a substituted or unsubstituted C1 to C10 alkyl group, a halogen atom, a halogen-containing group, or a combination thereof.

The monomer may have a molecular weight of about 200 to about 5,000. When the monomer has a molecular weight within the above range, solubility of the monomer having high carbon content in a solvent may be improved and an improved thin layer may be obtained through spin-on coating.

Hereinafter, a hardmask composition according to an example embodiment is described.

According to the present example embodiment, a hardmask composition includes a monomer according to an embodiment and a solvent.

The monomer is described above; one kind of the monomer may be used, or two or more kinds of the monomer may be mixed.

The solvent may be a suitable solvent having sufficient solubility or dispersion for the monomer and may be, for example, at least one selected from propylene glycol, propylene glycol diacetate, methoxy propanediol, diethylene glycol, diethylene glycol butylether, tri(ethylene glycol) monomethylether, propylene glycol monomethylether, propylene glycol monomethylether acetate, cyclohexanone, ethyllactate, gamma-butyrolactone, methylpyrrolidone, and acetylacetone.

The monomer may be included in an amount of about 0.1 to about 50 wt % based on the total amount of the hardmask composition. When the monomer is included in the above range, a desired thickness of a coated thin film may be obtained.

The hardmask composition may further include a surfactant.

The surfactant may include, for example, alkylbenzene sulfonate salt, alkyl pyridinium salt, polyethylene glycol, a quaternary ammonium salt, etc.

The surfactant may be included in an amount of about 0.001 to about 3 parts by weight based on 100 parts by weight of the hardmask composition. Within the amount range, the solubility may be secured while reducing or avoiding changes in the optical properties of the hardmask composition.

Hereafter, a method for forming a pattern by using the hardmask composition is described.

A method of forming a pattern according to an example embodiment includes providing a material layer on a substrate, applying a hardmask composition according to an embodiment, including a monomer according to an embodiment and solvent, on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The substrate may be, for example, a silicon wafer, a glass substrate, or a polymer substrate.

The material layer is a material to be finally patterned, for example, a metal layer such as an aluminum layer and a copper layer, a semiconductor layer such as a silicon layer, or an insulation layer such as a silicon oxide layer and a silicon nitride layer. The material layer may be formed through a method such as a chemical vapor deposition (CVD) process.

The hardmask composition may be applied by spin-on coating in a form of a solution. Herein, a thickness of the hardmask composition may be, for example, about 100 Å to about 10,000 Å.

The heat-treating the hardmask composition may be performed at, for example, about 100 to about 500° C. for about 10 seconds to 10 minutes. During heat-treating, the monomer may cause a self cross-linking and/or mutual cross-linking reaction.

The silicon-containing thin layer may be made of, for example, silicon nitride, silicon oxide, or silicon oxynitride (SiON).

The method may further include forming a bottom anti-reflective coating (BARC) on the silicon-containing thin layer. For example, a silicon oxynitride-containing thin layer may be formed on the hardmask layer, then a bottom antireflective coating is formed, and subsequently a photoresist layer is formed on the bottom antireflective coating.

Exposure of the photoresist layer may be performed using, for example, ArF, KrF, or EUV. After exposure, heat treatment may be performed at about 100° C. to about 500° C.

The etching process of the exposed part of the material layer may be performed through a dry etching process using an etching gas and the etching gas may be, for example, $CHF_3$, $CF_4$, $Cl_2$, $BCl_3$, a mixed gas thereof, etc.

The etched material layer may be formed in a plurality of patterns, and the plurality of patterns may be a metal pattern, a semiconductor pattern, an insulation pattern, and the like, for example diverse patterns of a semiconductor integrated circuit device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS OF MONOMER

Synthesis Example 1

30.2 g (0.1 mol) of benzoperylene and 95.9 g (0.5 mol) of 3-quinolinecarbonyl chloride along with 500 g of a mixed solution of chloroform/dichloromethane were put in a flask to prepare a solution. Subsequently, the solution was agitated and reacted at room temperature with a stirring bar, while 122.33 g (0.5 mol) of aluminum chloride was added little by little thereto.

When the reaction was complete, water was used to remove a reaction by-product and unreacted aluminum chloride. Subsequently, 108.0 g (0.534 mol) of 1-dodecanethiol, 35.9 g (0.640 mol) of potassium hydroxide (KOH), and 300 g of N,N-dimethylformamide were added to the obtained reactant as a powder, and the mixture was agitated at 120° C. for 8 hours. Subsequently, the mixture was cooled down and neutralized to pH 7 by using a 10% hydrogen chloride solution.

Then, the mixture was extracted with ethyl acetate and rotary-evaporated, the obtained powder was dissolved in 200 mL of tetrahydrofuran, and 18.98 g (0.5 mol) of lithium aluminum hydride was added little by little thereto for a reaction. When the reaction was complete, a mixture of water/methanol was used to remove a reaction by-product, obtaining a compound represented by the following Chemical Formula 1aa.

[Chemical Formula 1aa]

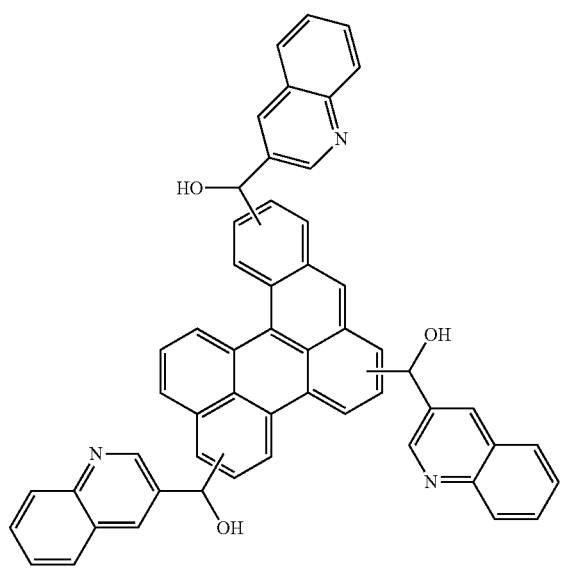

Synthesis Example 2

50.0 g (0.166 mol) of coronene and 97.3 g (0.499 mol) of 2H-chromene-3-carbonyl chloride were added to 700 g of a mixed solution of chloroform/dichloromethane in a flask to prepare a solution. Subsequently, the solution was agitated with a stirring bar, 66.6 g (0.499 mol) of aluminum chloride was little by little was added thereto, and the mixture was heated up to 60° C. and agitated for 8 hours.

When the reaction was complete, a precipitate produced by adding methanol thereto was filtered and subsequently, washed with a mixture of water/methanol mixture to remove a reaction by-product and unreacted aluminum chloride. 61.8 g (0.095 mol) of the dried reaction products, $K_4Fe(CN)_6$, (0.054 mol), a PS—Pd(II)-anthra catalyst (1.0 mol % of Pd), and triethylamine (0.11 mol) were dissolved in 300 ml of N,N-dimethylformamide, and the solution was agitated at 100° C. for 24 hours.

When the reaction was complete, the mixture was slowly cooled down to room temperature and then filtered to remove a PS—Pd (II)-anthra catalyst, and purified through flash column chromatography using silica gel. The obtained powder was dissolved in 300 mL of tetrahydrofuran, and 38 g (1.0 mol) of lithium aluminum hydride ($LiAlH_4$) was added little by little thereto for a reaction. When the reaction was complete, a mixture of water/methanol was used to remove a reaction by-product, obtaining a compound represented by the following Chemical Formula 1bb.

[Chemical Formula 1bb]

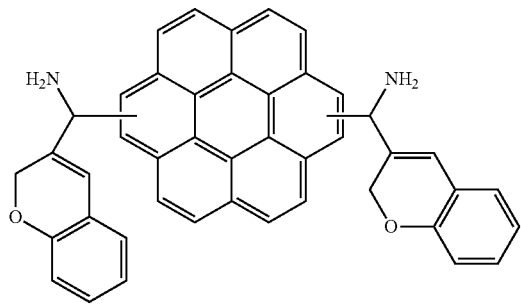

Synthesis Example 3

21.8 g (0.105 mol) of phenanthro[4,5-bcd]thiophene and 48.5 g (0.22 mol) of methoxy naphthoyl chloride were dissolved in 500 g of a chloroform/dichloromethane mixed solution. The solution was agitated with a stirring bar, and 61.2 g (0.35 mol) of aluminum chloride was added little by little thereto for a reaction.

When the reaction was complete, water was used to remove a reaction byproduct and unreacted aluminum chloride. The reactant obtained as powder was heated with 40 ml of formamide and 5 ml of 85% formic acid at 190° C. for 3 hours. The reactant was cooled down to a temperature of less than or equal to 100° C. and added to 250 ml of water at room temperature, and a precipitate produced therein was filtered and washed with a mixture of water/methanol mixture to remove a reaction by-product, obtaining a compound represented by the following Chemical Formula 1cc.

[Chemical Formula 1cc]

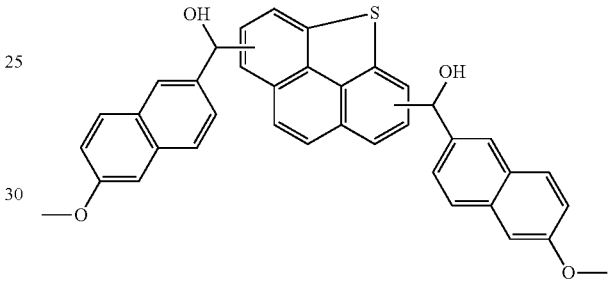

Synthesis Example 4

26.4 g (0.105 mol) of benzopyrene and 58.4 g (0.3 mol) of 2H-chromene-3-carbonyl chloride were put in 500 g of a mixed solution of chloroform/dichloromethane to prepare a solution. The solution was agitated with a stirring bar, and 40.0 g (0.3 mol) of aluminum chloride was added little by little thereto for a reaction.

When the reaction was complete, water was used to remove a reaction byproduct and unreacted aluminum chloride to obtain a reaction product as a powder, and the powder was filtered and dried. The dried powder along with 95.9 g (0.5 mol) of 3-quinolinecarbonyl chloride was added to and 500 g of a mixed solution of chloroform/dichloromethane, 122.33 g (0.5 mol) of aluminum chloride was added little by little thereto while the mixture was agitated with a stirring bar, and the resulting mixture was heated up to 60° C. and reacted for 12 hours.

When the reaction was complete, the reactant was extracted with ethyl acetate after removing a reaction byproduct and unreacted aluminum chloride by using water, and the extract was dried under a reduced pressure. 270 g of dimethylformamide was added to the produced compound in a 1 L flask, and 37.83 g (1 mol) of sodium borohydride ($NaBH_4$) was added little by little thereto. When the addition was complete, the mixture was agitated for a reaction at 50° C. for 18 hours. When the reaction was complete, the resultant was neutralized to about pH 6 with 7% hydrogen chloride, extracted with ethyl acetate, and dried through rotary evaporation, obtaining a compound represented by the following Chemical Formula 1dd.

[Chemical Formula 1dd]

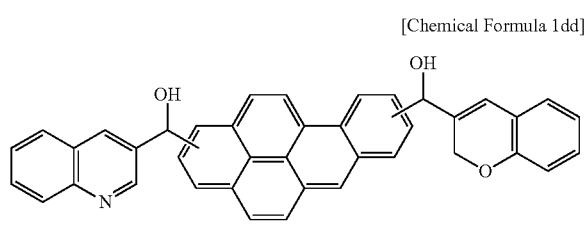

Synthesis Example 5

First Step: Friedel-Crafts Acylation Reaction 28.0 g (0.1345 mol) of 1,4-cyclohexanedicarbonyldichloride, 62.4 g (0.269 mol) of methoxypyrene, and 496 g of 1,2-dichloroethane were put in a flask to prepare a solution. Subsequently, 17.9 g (0.1345 mol) of aluminum chloride was slowly added to the solution, and the mixture was agitated at room temperature for 12 hours. When the reaction was complete, a precipitate produced by adding methanol thereto was filtered and dried.

Second Step: Demethylation Reaction 6.00 g (0.01001 mol) of the compound, 10.13 g (0.05005 mol) of 1-dodecanethiol, 3.37 g (0.06006 mol) of potassium hydroxide, and 30.3 g of N,N-dimethylformamide were put in a flask and agitated at 120° C. for 8 hours. Subsequently, the mixture was cooled down and neutralized to pH 6-7 with a 5% hydrochloric acid solution, and a precipitate produced therein was filtered and dried.

Third Step: Reduction Reaction 4.00 g (0.00699 mol) of the compound and 28.5 g of tetrahydrofuran were put in a flask to prepare a solution. 5.29 g (0.1398 mol) of a sodium borohydride aqueous solution was slowly added to the solution, and the mixture was agitated at room temperature for 24 hours. When the reaction was complete, the reactant was neutralized to pH 7 with a 5% hydrochloric acid solution and extracted with ethyl acetate, and the extract was dried, obtaining a compound represented by Chemical Formula 1ee.

[Chemical Formula 1ee]

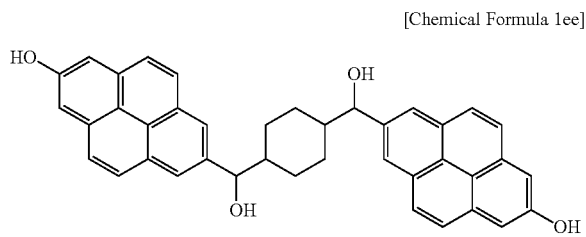 [SMILES: Oc1cc2ccc3cc(C(O)C4CCC(C(O)c5cc6ccc7cc(O)cc8ccc(c5)c6c78)CC4)cc4ccc(c1)c2c34]

Synthesis Example 6

First Step: Friedel-Crafts Acylation Reaction 39.44 g (0.269 mol) of cyclohexanecarbonylchloride, 62.4 g (0.269 mol) of pyrene, and 523 g of 1,2-dichloroethane were put in a flask to prepare a solution. 35.8 g (0.269 mol) of aluminum chloride was slowly added to the solution, and the mixture was agitated at room temperature for 12 hours. When the reaction was complete, a precipitate produced by adding methanol thereto was filtered and dried.

45 g (0.144 mol) of the compound, 24.6 g (0.144 mol) of p-methoxybenzoyl chloride, and 467 g of 1,2-dichloroethane were put in a flask to prepare a solution. 19.2 g (0.144 mol) of aluminum chloride was slowly added to the solution, and the mixture was agitated at room temperature for 12 hours. When the reaction was complete, a precipitate produced by adding methanol thereto was filtered and dried.

Second Step: Demethylation Reaction 8.93 g (0.02 mol) of the compound, 20.26 g (0.1 mol) of 1-dodecanethiol, 6.74 g (0.12 mol) of potassium hydroxide, and 30.3 g of N,N-dimethylformamide were put in a flask and agitated at 120° C. for 8 hours. Subsequently, the mixture was cooled down and neutralized to about pH 6-7 with a 5% hydrochloric acid solution, and a precipitate produced therein was filtered and dried.

Third Step: Reduction Reaction 6.05 g (0.014 mol) of the compound and 37.4 g of tetrahydrofuran were put in a flask to prepare a solution. 10 g (0.28 mol) of a sodium borohydride aqueous solution was slowly added to the solution, and the mixture was agitated at room temperature for 24 hours. When the reaction was complete, the reactant was neutralized to about pH 7 by using a 5% hydrochloric acid solution and extracted with ethyl acetate, and the extract was dried, obtaining a compound represented by Chemical Formula 1ff.

[Chemical Formula 1ff]

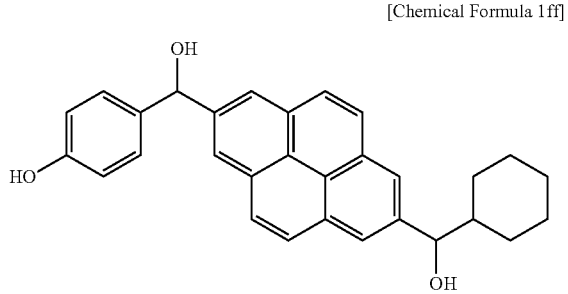 [SMILES: Oc1ccc(C(O)c2cc3ccc4cc(C(O)C5CCCCC5)cc5ccc(c2)c3c45)cc1]

Synthesis Example 7

First Step: Friedel-Crafts Acylation Reaction 19.7 g (0.1345 mol) of cyclohexanoyl chloride, 24.7 g (0.1345 mol) of tertiary-butylmethoxythiophene-2-carboxylate, and 236 g of 1,2-dichloroethane were put in a flask to prepare a solution. 17.9 g (0.1345 mol) of aluminum chloride was slowly added to the solution, and the mixture was agitated at room temperature for 12 hours. When the reaction was complete, a precipitate produced by adding methanol thereto was filtered and dried.

Second Step: Removal Reaction of Tertiary-Butyl Group 17 g (0.06 mol) of the compound was dissolved in 240 mL of dioxane in a flask, 4.95 g (0.12 mol) of lithium hydroxide monohydrate dissolved in 240 mL of water was added thereto, and the mixture was agitated at room temperature for 18 hours. Then, the reactant was acidified in pH 3 with a 2 M HCl aqueous solution and dried under a reduced pressure. Subsequently, the material was washed with a mixed solution of ethanol, water, and brine and dried.

Third Step: Chlorination Reaction 8 g (0.034 mol) of the compound was dissolved in 118.9 mL (1.51 mol) of thionyl chloride in a flask, and the solution was refluxed under a nitrogen atmosphere for 3 hours. The thionyl chloride left after the reaction was dried and removed under a reduced pressure.

Fourth Step: Friedel-Crafts Acylation Reaction 5.0 g (0.0195 mol) of the compound, 4.5 g (0.0195 mol) of methoxypyrene, and 38 g of 1,2-dichloroethane were put in a flask to prepare a solution. Subsequently, 2.6 g (0.0195 mol) of aluminum chloride was slowly added to the solution, and the mixture was agitated at room temperature for 12 hours. When the reaction was complete, a precipitate produced by adding methanol thereto was filtered and dried.

Fifth Step: Demethylation Reaction 6.00 g (0.0132 mol) of the compound, 2.67 g (0.0132 mol) of 1-dodecanethiol, 0.74 g (0.0132 mol) of potassium hydroxide, and 10.1 g of N,N-dimethylformamide were put in a flask and agitated at 120° C. for 8 hours. Subsequently, the mixture was cooled down and neutralized to about pH 6-7 by using a 5% hydrochloric acid solution, and a precipitate produced therein was filtered and dried.

Sixth Step: Reduction Reaction 4.00 g (0.00913 mol) of the compound and 32.4 g of tetrahydrofuran were put in a flask to prepare a solution. 6.94 g (0.1826 mol) of a sodium borohydride aqueous solution was slowly added to the solution, and the solution was agitated at room temperature for 24 hours. When the reaction was complete, the reactant was neutralized to about pH 7 with a 5% hydrochloric acid solution and extracted with ethyl acetate, and the extract was dried, obtaining a compound represented by Chemical Formula 1gg.

[Chemical Formula 1gg]

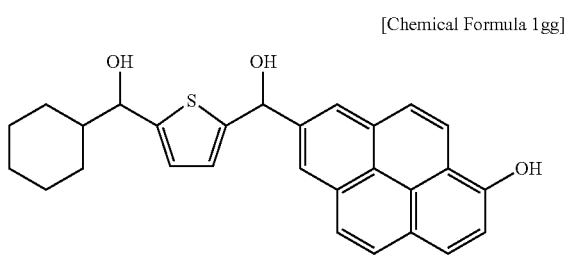 [SMILES: Oc1ccc2ccc3cc(C(O)c4ccc(C(O)C5CCCCC5)s4)cc4ccc1c2c34]

Synthesis Example 8

First Step: Friedel-Crafts Acylation Reaction 9.5 g (0.054 mol) of 4-methoxycyclohexane-1-carbonylchloride, 6.24 g (0.027 mol) of pyrene, and 53 g of 1,2-dichloroethane were put in a flask to prepare a solution. 3.6 g (0.027 mol) of aluminum chloride was slowly added to the solution, and the mixture was agitated at room temperature for 12 hours. When the reaction was complete, a precipitate produced by adding methanol thereto was filtered and dried.

Second Step: Demethylation Reaction 9.65 g (0.02 mol) of the compound and 6 g (0.04 mol) of sodium iodide were dissolved in 50 mL of acetonitrile in a flask, and 10.84 g (0.04 mol) of trifluorinated boron etherate was injected thereinto with a predetermined pressure. Subsequently, the mixture was agitated at room temperature for 8 hours. The mixture was agitated with 50 mL of a sodium bicarbonate aqueous solution, and the resulting mixture was extracted with 30 mL of ether. An organic layer produced therein was washed with 40 mL of a sodium thiosulfite aqueous solution and 100 mL of water and then dried.

Third Step: Reduction Reaction 4.5 g (0.01 mol) of the compound and 17.4 g of tetrahydrofuran were put in a flask to prepare a solution. 7.1 g (0.2 mol) of a sodium borohydride aqueous solution was slowly added to the solution, and the mixture was agitated at room temperature for 24 hours. When the reaction was complete, the reactant was neutralized to about pH 7 with a 5% hydrochloric acid solution and extracted with ethyl acetate, and the extract was dried, obtaining a compound represented by Chemical Formula 1hh.

[Chemical Formula 1hh]

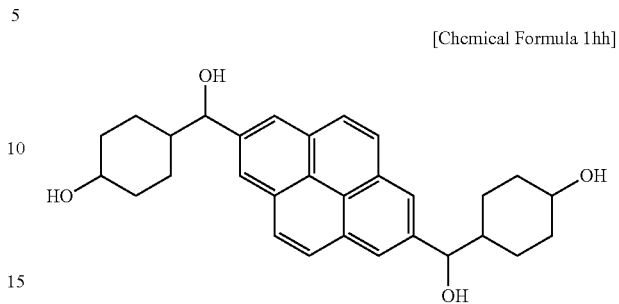

Synthesis Example 9

First step: Friedel-Crafts Acylation Reaction 39.44 g (0.269 mol) of thiophene-3-carbonylchloride, 62.4 g (0.269 mol) of pyrene, and 523 g of 1,2-dichloroethane were put in a flask to prepare a solution. 35.8 g (0.269 mol) of aluminum chloride was slowly added to the solution, and the mixture was agitated at room temperature for 12 hours. When the reaction was complete, a precipitate produced by adding methanol thereto was filtered and dried.

45 g (0.144 mol) of the compound, 25.3 g (0.144 mol) of 4-methoxycyclohexane-1-carbonylchloride, and 467 g of 1,2-dichloroethane were put in a flask to prepare a solution. 19.2 g (0.144 mol) of aluminum chloride was slowly added to the solution, and the mixture was agitated at room temperature for 12 hours. When the reaction was complete, a precipitate produced by adding methanol thereto was filtered and dried.

Second Step: Demethylation Reaction 9.05 g (0.02 mol) of the compound, 20.26 g (0.1 mol) of 1-dodecanethiol, 6.74 g (0.12 mol) of potassium hydroxide, and 30.3 g of N,N-dimethylformamide were put in a flask and agitated at 120° C. for 8 hours. The mixture was cooled down and neutralized to about pH 6-7 with a 5% hydrochloric acid solution, and a precipitate produced therein was filtered and dried.

Third Step: Reduction Reaction 6.14 g (0.014 mol) of the compound and 37.4 g of tetrahydrofuran were put in a flask to prepare a solution. 10 g (0.28 mol) of a sodium borohydride aqueous solution was slowly added to the solution, and the mixture was agitated at room temperature for 24 hours. When the reaction was complete, the reactant was neutralized to about pH 7 with a 5% hydrochloric acid solution and extracted, and the extract was dried, obtaining a compound represented by Chemical Formula 1ii.

[Chemical Formula 1ii]

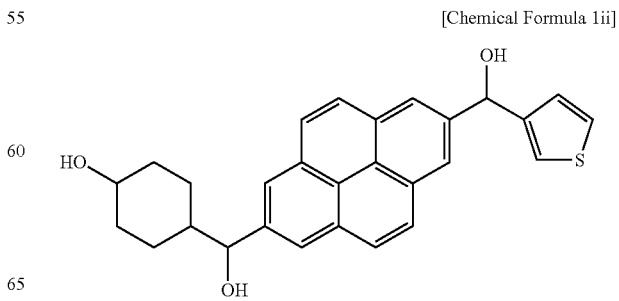

Synthesis Example 10

First Step: Friedel-Crafts Acylation Reaction 22.6 g (0.1345 mol) of dimethylmalonyl chloride, 62.4 g (0.269 mol) of methoxypyrene, and 556 g of 1,2-dichloroethane were put in a flask to prepare a solution. Subsequently, 17.9 g (0.1345 mol) of aluminum chloride was slowly added to the solution, and the mixture was agitated at room temperature for 12 hours. When the reaction was complete, a precipitate produced by adding methanol thereto was filtered and dried.

Second Step: Demethylation Reaction 5.60 g (0.01001 mol) of the compound, 10.13 g (0.05005 mol) of 1-dodecanethiol, 3.37 g of (0.06006 mol) of potassium hydroxide, and 27.6 g of N,N-dimethylformamide were put in a flask and agitated at 120° C. for 8 hours. Subsequently, the mixture was cooled down and neutralized to about pH 6-7 with a 5% hydrogen chloride solution, and a precipitate produced therein was filtered and dried.

Third Step: Reduction Reaction 2.19 g (0.004120 mol) of the compound and 28.5 g of tetrahydrofuran were put in a flask to prepare a solution. 3.12 g (0.08240 mol) of a sodium borohydride aqueous solution was slowly added to the solution, and the mixture was agitated at room temperature for 24 hours. When the reaction was complete, the reactant was neutralized to about pH 7 with a 5% hydrogen chloride solution and extracted with ethyl acetate, and the extract was dried, obtaining a compound represented by Chemical Formula 1jj.

[Chemical Formula 1jj]

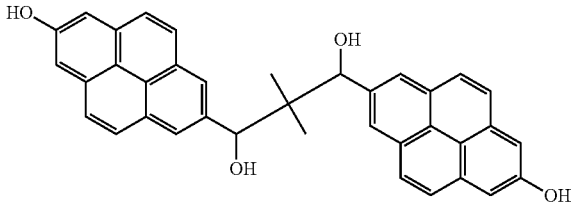

Synthesis Example 11

First Step: Friedel-Crafts Acylation Reaction 20.4 g (0.1345 mol) of fumaryl chloride, 62.4 g (0.269 mol) of methoxypyrene, and 530 g of 1,2-dichloroethane were put in a flask to prepare a solution. 17.9 g (0.1345 mol) of aluminum chloride was slowly added to the solution, and the mixture was agitated for a reaction at room temperature for 12 hours. When the reaction was complete, a precipitate produced by adding methanol thereto was filtered and dried.

Second Step: Demethylation Reaction 5.44 g (0.01001 mol) of the compound, 10.13 g (0.05005 mol) of 1-dodecanethiol, 3.37 g (0.06006 mol) of potassium hydroxide, and 27.3 g of N,N-dimethylformamide were put in a flask and agitated at 120° C. for 8 hours. The reaction mixture was cooled down and neutralized to about pH 6-7 with a 5% hydrogen chloride solution, and a precipitate produced therein was filtered and dried.

Third Step: Reduction Reaction 2.06 g (0.004120 mol) of the compound and 28.5 g of tetrahydrofuran were put in a flask to prepare a solution. 3.12 g (0.08240 mol) of a sodium borohydride aqueous solution was slowly added to the solution, and the mixture was agitated at room temperature for 24 hours. When the reaction was complete, the reactant was neutralized to about pH 7 with a 5% hydrogen chloride solution and extracted with ethyl acetate, and the extract was dried, obtaining a compound represented by Chemical Formula 1kk.

[Chemical Formula 1kk]

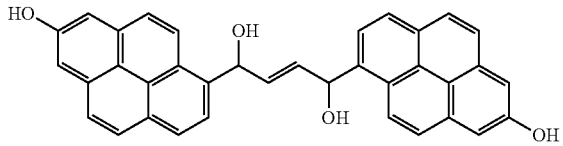

Synthesis Example 12

27.6 g (0.1 mol) of benzoperylene, 48.5 g (0.22 mol) of methoxy naphthoyl chloride, and 500 g of a chloroform/dichloromethane mixed solution were put in a flask to prepare a solution. While the solution was agitated with a stirring bar, 61.2 g (0.35 mol) of aluminum chloride was added little by little thereto for a reaction.

When the reaction was complete, water was used to remove a reaction byproduct and unreacted aluminum chloride. The reaction product obtained as a powder along with 40 ml of formamide and 5 ml of 85% formic acid was refluxed at 190° C. for 3 hours. Subsequently, the reactant was cooled down to less than or equal to 100° C. and added to 250 ml of water at room temperature, and a precipitate produced therein was filtered, washed with a mixture of water/methanol mixture to remove a reaction by-product, obtaining a compound represented by the following Chemical Formula 1ll.

[Chemical Formula 1ll]

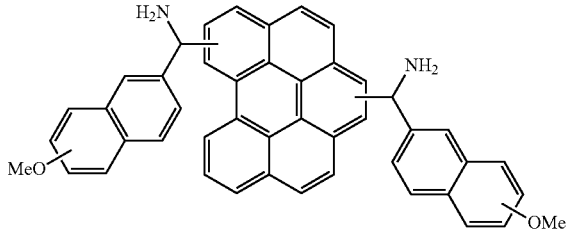

Synthesis Example 13

50.0 g (0.166 mol) of coronene, 83 g (0.499 mol) of 4-iodobenzoylchloride, and 700 g of a mixed solution of chloroform/dichloromethane were put in a flask to prepare a solution. While the solution was agitated with a stirring bar, 66.6 g (0.499 mol) of aluminum chloride was added little by little thereto, and the mixture was heated up to 60° C. and agitated for 8 hours.

When the reaction was complete, a precipitate produced by adding methanol thereto was filtered and washed with a mixture of water/methanol mixture to remove a reaction byproduct and unreacted aluminum chloride. 80.2 g (0.081 mol) of the dried reaction products, 0.054 mol of $K_4Fe(CN)_6$, a PS—Pd (II)-anthra catalyst (1.0 mol % of Pd), and 0.11 mol of triethylamine were dissolved in 300 ml of N,N-dimethylformamide, and subsequently, the solution was agitated at 100° C. for 24 hours. When the reaction was complete, the reactant was slowly cooled down to room temperature and filtered to remove the PS—Pd (II)-anthra catalyst, and the filtered solution was purified through flash column chromatography using silica gel. The obtained powder was dissolved in 300 mL of tetrahydrofuran, and 38 g (1.0 mol) of lithium aluminum hydride (LiAlH$_4$) was added little by little thereto for a reaction. When the reaction was complete, a mixture of water/methanol was used to remove a reaction by-product, obtaining a compound represented by the following Chemical Formula 1mm-1.

[Chemical Formula 1mm-1]

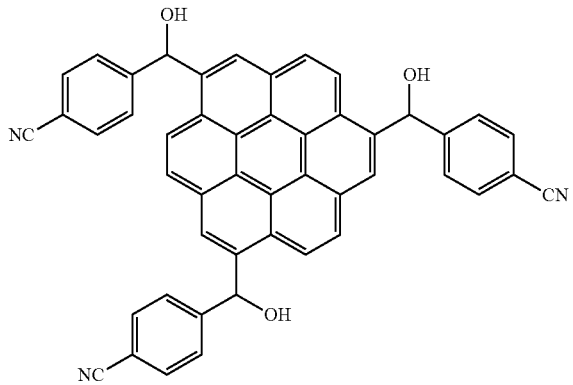

Synthesis Example 14

28.2 g (0.1 mol) of methoxybenzopyrene, 23.5 g (0.11 mol) of methoxy naphthoyl chloride, and 500 g of a mixed solution of chloroform/dichloromethane were put in a flask to prepare a solution. While the solution was agitated with stirring bar, 36.7 g (0.15 mol) of aluminum chloride was added little by little thereto for a reaction at room temperature.

One hour later, 21 g (0.11 mol) of naphthoyl chloride was added to the reactant, and 36.7 g (0.15 mol) of aluminum chloride was additionally added thereto. When the reaction was complete, water was used to remove a reacting byproduct and unreacted aluminum chloride. 108.0 g (0.534 mol) of 1-dodecanethiol, 35.9 g (0.640 mol) of potassium hydroxide (KOH), and 300 g of N,N-dimethylformamide were added to the obtained reactant as powder, and the mixture was agitated at 120° C. for 8 hours. Subsequently, the mixture was cooled down and neutralized to about pH 7 by using a 10% hydrogen chloride solution. Then, the reactant was extracted with ethyl acetate and rotary-evaporated, the obtained powder was dissolved in 200 mL of tetrahydrofuran, and 18.98 g (0.5 mol) of lithium aluminum hydride was added little by little thereto for a reaction. When the reaction was complete, a mixture of water/methanol was used to remove a reaction by-product, obtaining a compound represented by the following Chemical Formula 1nn.

[Chemical Formula 1nn]

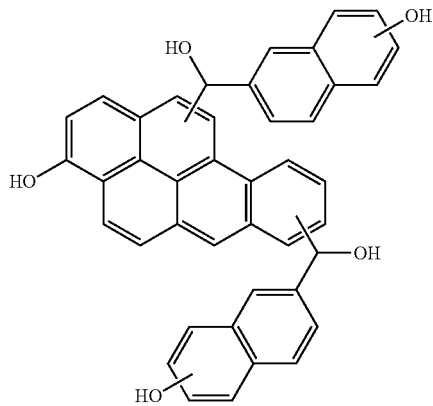

Synthesis Example 15

26.5 g (0.105 mol) of perylene, 10.15 g (0.05 mol) of isophthaloyl chloride, and 500 g of a mixed solution of chloroform/dichloromethane were put in a flask to prepare a solution. While the solution was agitated with a stirring bar, 29.33 g (0.22 mol) of aluminum chloride was added little by little thereto for a reaction. The mixture was reacted in an ice bath for 2 hours to control exothermic characteristics.

When the reaction was complete, water was used to remove a reaction byproduct and unreacted aluminum chloride, and a reaction product obtained as powder was filtered and dried. The dried powder and 270 g of dimethylformamide were put in a flask, 37.83 g (1 mol) of sodium borohydride (NaBH$_4$) was added little by little thereto, and the mixture was agitated at 50° C. for 18 hours, when the addition was complete. When the reaction was complete, the reactant was neutralized to about pH 6 by using a 7% hydrogen chloride solution and extracted with ethyl acetate, and the extract was dried through rotary evaporation. The dried powder was dissolved in 400 ml of dichloromethane, and the solution was maintained in an ice bath at 0° C. 0.10 mol of 1,8-diazabicycloundec-7-ene was slowly added thereto, a solution prepared by dissolving 0.08 mol of p-toluene sulfonylchloride in 200 ml of dichloromethane was slowly added thereto, and the ice bath was slowly removed to increase the temperature of the mixture up to room temperature. The mixture was reacted at the room temperature for 30 minutes, the reactant was several times respectively washed with 5% hydrochloric acid and a 10% sodium bicarbonate aqueous solution to remove a reaction byproduct to obtain an organic layer, and a monomer represented by the following Chemical Formula 1oo was obtained from the organic layer.

[Chemical Formula 1oo]

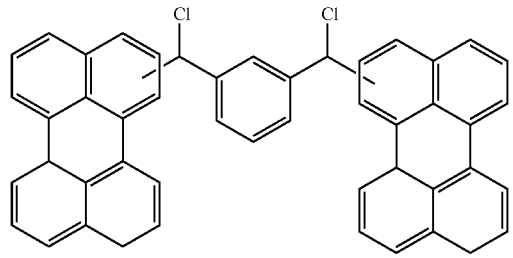

Synthesis Example 16

50.0 g (0.166 mol) of coronene, 93 g (0.499 mol) of 1-(4-methylthio)-benzoyl chloride, and 700 g of a mixed solution of chloroform/dichloromethane were put in a flask to prepare a solution. While the solution was agitated with a stirring bar, 66.6 g (0.499 mol) of aluminum chloride was added little by little thereto, and the mixture was heated up to 60° C. for 8 hours.

When the reaction was complete, a precipitate produced therein by adding methanol thereto was filtered and washed with a mixture of water/methanol to remove a reaction byproduct and unreacted aluminum chloride. 183.6 g (0.908 mol) of 1-dodecanethiol, 61.0 g (1.09 mol) of potassium hydroxide, and 500 g of N,N-dimethylformamide were added to the dried reaction product, and the mixture was agitated at 120° C. for 8 hours. Subsequently, the mixture was cooled down, neutralized to pH 7 with a 10% hydrogen chloride solution, extracted with ethyl acetate, and dried through rotary evaporation, the obtained powder was dissolved in 300 mL of tetrahydrofuran, and the solution was reacted while 32.3 g (0.85 mol) 32.3 g of lithium aluminum hydride was added little by little thereto for a reaction. When the reaction was complete, a mixture of water/methanol was used to remove a reaction by-product, obtaining a compound represented by the following Chemical Formula 1mm-2.

[Chemical Formula 1mm-2]

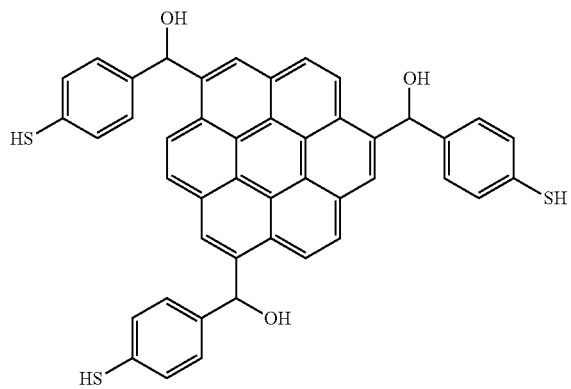

Comparative Synthesis Example 1

42 g (0.166 mol) of perylene and 95.3 g (0.499 mol) of naphthoylchloride were put in 700 g of a mixed solution of chloroform/dichloromethane to prepare a solution. While the solution was agitated with a stirring bar, 66.6 g (0.499 mol) of aluminum chloride (AlCl$_3$) was added little by little thereto, and the mixture was heated up to 60° C. and reacted for 8 hours.

When the reaction was complete, a precipitate produced by adding methanol thereto was filtered and washed with a mixture of water/methanol to remove a reaction byproduct and unreacted aluminum chloride. 57.6 g (0.105 mol) of the dried reaction product and 200 g of Raney nickel were refluxed and agitated with 600 ml of 2-propanol for 1 hour. When the reaction was complete, the reactant was cooled down to room temperature, and subsequently, an organic layer produced therein was removed and dried through rotary evaporation, obtaining a compound represented by the following Chemical Formula 2.

[Chemical Formula 2]

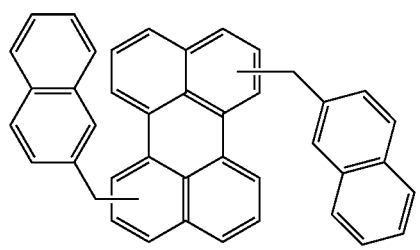

Comparative Synthesis Example 2

First Step: Friedel-Crafts Acylation Reaction 50.0 g (0.166 mol) of coronene, 46.8 g (0.333 mol) of benzoylchloride, and 330 g of 1,2-dichloroethane were put in a flask to prepare a solution. Subsequently, 44.4 g (0.333 mol) of aluminum chloride was slowly added to the solution at room temperature, and the mixture was heated up to 60° C. and agitated for 8 hours. When the reaction was complete, a precipitate produced by adding methanol was filtered and dried.

Second Step: Reduction Reaction 25.0 g (0.0492 mol) of the prepared compound and 174 g of tetrahydrofuran were put in a flask. Subsequently, 18.6 g (0.492 mol) of a sodium borohydride aqueous solution was slowly added to the solution, and the mixture was agitated at room temperature for 24 hours. When the reaction was complete, the reactant was neutralized to pH 7 with a 5% hydrogen chloride solution, extracted with ethyl acetate, and dried, obtaining a compound represented by the following Chemical Formula 3.

[Chemical Formula 3]

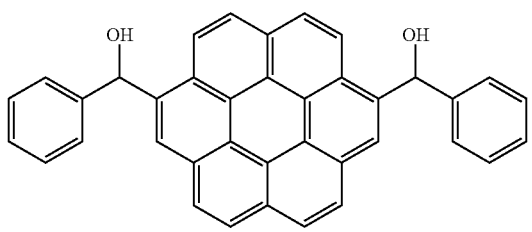

Comparative Synthesis Example 3

10 g (0.057 mol) of benzylmethacrylate and 10.6 g (0.057 mol) of cyclohexylmethacrylate were mixed with 41 g of methylethylketone in a flask under a nitrogen atmosphere. Then, 2.6 g of dimethyl-2,2'-azobis(2-methylpropionate) as a polymerization initiator was added to the mixture at 80° C. for 4 hours with a syringe, and the mixture was additionally agitated. When the polymerization was complete, the obtained polymer was slowly precipitated in the excessive amount of a hexane solvent. Accordingly, the precipitate was filtered and then dissolved in the appropriate amount of a mixed solvent of hexane/isopropanol, and the solution was agitated. Subsequently, the obtained precipitate was dried in a vacuum oven at 50° C. for about 24 hours, obtaining a compound represented by Chemical Formula 4.

The obtained polymer had a weight average molecular weight (Mw) of 6200 and polydispersity (Mw/Mn) of 1.45.

[Chemical Formula 4]

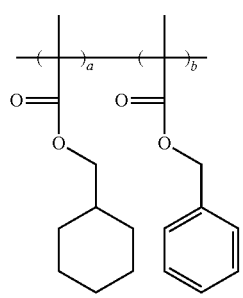

(In the above Chemical Formula 4, a:b=1:1)

Comparative Synthesis Example 4

50.0 g (0.166 mol) of coronene, 70 g (0.499 mol) of benzoyl chloride, and 700 g of a mixed solution of chloroform/dichloromethane were put in a flask to prepare a solution. The solution was agitated with a stirring bar, 66.6 g (0.499 mol) of aluminum chloride ($AlCl_3$) was added little by little thereto, and the mixture was heated up to 60° C. and agitated for 8 hours.

When the reaction was complete, a precipitate was produced by adding methanol thereto was filtered and washed with a mixture of water/methanol to remove a reaction product and unreacted aluminum chloride. 62.5 g (0.102 mol) of the dried reaction product and 200 g of Raney nickel were refluxed and agitated with 600 ml of 2-propanol for 1 hour. When the reaction was complete, the reactant was cooled down to room temperature, and subsequently, an organic layer produced therein was removed and dried through rotary evaporation, obtaining a compound represented by the following Chemical Formula 5.

[Chemical Formula 5]

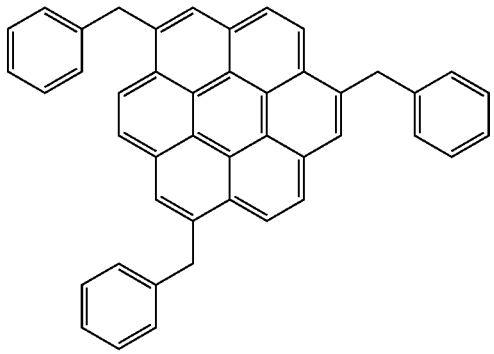

Preparation of Hard Mask Composition

Example 1

The compound according to Synthesis Example 1 was dissolved in a mixed solvent of propylene glycolmonomethylether acetate (PGMEA) and cyclohexanone (7:3 (v/v)), and the solution was filtered to prepare a hardmask composition. The compound was adjusted to be included in an amount of 10.0 wt % or 13.0 wt % depending on the total weight of the hardmask composition depending on a desired thickness.

Examples 2 to 16

Each hardmask composition was prepared according to the same method as Example 1 except for respectively using the monomers according to Synthesis Examples 2 to 16 instead of the monomer according to Synthesis Example 1.

Comparative Examples 1 to 4

Each hardmask composition was prepared according to the same method as Example 1 except for respectively using the monomers according to Comparative Synthesis Examples 1 to 4 instead of the monomer according to Synthesis Example 1.

Evaluation 1: Etch Resistance

The hardmask composition (monomer content: 10.0 wt % based on the total composition) according to Examples 1 to 4 and Comparative Example 1 were respectively spin-on coated on a silicon wafer and heat-treated on a hot plate at 240° C. for 1 minute to form a thin film. Thickness of the thin films was measured by using a thin film thickness measurement device made by K-MAC.

Subsequently, the thin films were dry etched by using a $CF_x$ mixed gas for 100 seconds, their thickness was measured, and their bulk etch rate (BER) was calculated according to the following Calculation Equation 1.

(initial thin film thickness−thin film thickness after etching)/etching time (Å/s)  [Calculation Equation 1]

The results are provided in Table 1-1.

TABLE 1-1

|  | Initial thin film thickness (Å) | Thin film thickness after etching (Å) | Etch rate (Å/sec) |
|---|---|---|---|
| Comparative Example 1 | 4853 | 3630 | 25.2 |
| Example 1 | 4763 | 3585 | 24.7 |
| Example 2 | 4586 | 3447 | 24.8 |
| Example 3 | 4618 | 3482 | 24.5 |
| Example 4 | 4693 | 3542 | 24.5 |

Referring to Table 1-1, the hardmask compositions according to Examples 1 to 4 showed a lower etch rate than the hardmask composition according to Comparative Example 1.

Accordingly, without being bound by theory, it is believed that the hardmask compositions according to Examples 1 to 4 had higher cross-linking and, thus, showed higher etch resistance than the hardmask composition according to Comparative Example 1.

The hardmask compositions (monomer content: 13.0 wt % based on the total composition) according to Examples 5 to 10 and Comparative Example 3 were respectively spin-on coated on a silicon wafer and heat-treated on a hot plate at 400° C. for 2 minutes. Subsequently, thickness of the thin films was measured. Subsequently, the thin films were dry etched by using a $N_2/O_2$ mixed gas and a $CF_x$ gas respectively for 60 seconds and 100 seconds, and then thickness of the thin films were measured again. The thicknesses of the thin films before and after the dry etching and etching time were used to calculate a bulk etch rate (BER) according to the following Calculation Equation 1.

The results are provided in Table 1-2.

TABLE 1-2

|  | Etch rate ($N_2/O_2$) (Å/sec) | Etch rate ($CF_x$) (Å/sec) |
|---|---|---|
| Example 5 | 24.5 | 28.1 |
| Example 6 | 24.3 | 27.3 |
| Example 7 | 24.5 | 28.8 |
| Example 8 | 24.9 | 28.9 |
| Example 9 | 24.7 | 28.9 |
| Example 10 | 24.5 | 28.8 |
| Comparative Example 3 | 29.7 | 32.4 |

Referring to Table 1-2, the thin films formed of the hardmask compositions according to Examples 5 to 10 showed a lower etch rate than the thin films formed of the hardmask composition according to Comparative Example 3.

Accordingly, without being bound by theory, it is believed that the hardmask compositions according to Examples 5 to 10 had higher cross-linking and, thus, higher etch resistance than the hardmask composition according to Comparative Example 3.

The hardmask compositions including 13 wt % of a monomer according to Examples 12 to 16 and Comparative Example 4 were respectively spin-on coated on a silicon wafer and heat-treated on a hot plate at 240° C. for 1 minute. Thickness of the thin films was measured by using a thin film thickness measurement device made by K-MAC.

Subsequently, the thin films were dry etched by using a $N_2/O_2$ mixed gas for 60 seconds, thicknesses of the thin films was measured, and etch rates were calculated based on the thickness.

The results are provided in Table 1-3.

TABLE 1-3

|  | Initial thin film thickness (Å) | Thin film thickness after etching (Å) | Etch rate (Å/sec) |
|---|---|---|---|
| Example 12 | 4525 | 3055 | 24.5 |
| Example 13 | 4351 | 2941 | 23.5 |
| Example 14 | 4792 | 3406 | 23.1 |
| Example 15 | 4295 | 2897 | 23.3 |
| Example 16 | 4777 | 3403 | 22.9 |
| Comparative Example 4 | 4478 | 2936 | 25.7 |

Referring to Tables 1-3, the hardmask composition according to Examples 12 to 16 showed a lower etch rate than the hardmask composition according to Comparative Example 4.

Accordingly, without being bound by theory, it is believed that the hardmask compositions according to Examples 12 to 16 had a higher cross-linking and showed a higher etch resistance than the hardmask composition according to Comparative Example 4.

Evaluation 2: Contact Angle Characteristics

The hardmask compositions (monomer content: 10.0 wt % based on the total composition) according to Examples 1 to 4 and Comparative Example 1 were respectively coated on a silicon wafer with a spinner. Subsequently, the hardmask compositions were baked on a hot plate at 400° C. for 120 seconds to form each thin film. Then, contact angle of the thin films was measured by using a contact angle measurement device, and coating property of the thin films was checked by the thin film thickness measurement device made by K-MAC.

The results are provided in Table 2.

TABLE 2

|  | Contact angle | Coating properties |
|---|---|---|
| Comparative Example 1 | 64 | Bad-generation of pin holes |
| Example 1 | 47 | Good |
| Example 2 | 50 | Good |
| Example 3 | 51 | Good |
| Example 4 | 49 | Good |

Referring to Table 2, the thin films made of the hardmask compositions according to Examples 1 to 4 showed a smaller contact angle than the thin film formed of the hardmask composition according to Comparative Example 1. Without being bound by theory, it is believed that the hardmask compositions according to Examples 1 to 4 were more hydrophilic and, thus, showed better coating property with a silicon wafer than the hardmask composition according to Comparative Example 1.

Evaluation 3: Gap-Fill and Planarization Characteristics

The hardmask compositions (monomer content: 10.0 wt % based on the total composition) according to Examples 1 to 4 and Comparative Example 1 were respectively spin-coated on a silicon wafer having a pattern and heat-treated on a hot plate at 400° C. for 120 seconds, and a field emission electron-scanning electronic microscope (FE-SEM) equipment was used to examine gap-fill and planarization characteristics.

The gap-fill characteristics was evaluated by examining if a void was generated or not on the cross section of the pattern with FE-SEM, and the planarization characteristics were evaluated by measuring a thickness of the hardmask layer from the image of the pattern cross section examined with FE-SEM and using it according to Calculation Equation 2 in FIG. 1. The planarization characteristics were better as a difference between $h_1$ and $h_2$ was smaller.

The results are provided in Table 3-1.

TABLE 3-1

|  | Gap-fill characteristics (Void) | | Planarization characteristics |
|---|---|---|---|
|  | Aspect ratio (1:1.5) | Aspect ratio (1:10) | main coating (1500 rpm) |
| Comparative Example 1 | No void | Void occurs | 24.55 |
| Example 1 | No void | No void | 21.57 |
| Example 2 | No void | No void | 22.62 |
| Example 3 | No void | No void | 23.83 |
| Example 4 | No void | No void | 21.95 |

Referring to Table 3-1, the thin films made of the hardmask compositions according to Examples 1 to 4 showed excellent planarization degree and no void and, thus, excellent gap-fill characteristics compared with the thin film formed of the hardmask composition according to Comparative Example 1.

The hardmask compositions (monomer content: 13 wt % based on the total composition) according to Examples 5 to 11 and Comparative Examples 2 and 3 were spin-coated on a silicon wafer having a pattern and heat-treated on a hot plate at 400° C. for 120 seconds, and a field emission electron-scanning electronic microscope (FE-SEM) equipment was used to examine gap-fill and planarization characteristics. The evaluation was performed as aforementioned.

The results are provided in Table 3-2.

TABLE 3-2

|  | Planarization characteristics | Gap-fill characteristics |
|---|---|---|
| Example 5 | 8% or less | No void |
| Example 6 | 8% or less | No void |
| Example 7 | 8% or less | No void |
| Example 8 | 8% or less | No void |
| Example 9 | 8% or less | No void |
| Example 10 | 8% or less | No void |
| Example 11 | 8% or less | No void |
| Comparative Example 2 | 15% or more and 20% or less | Void occurred |
| Comparative Example 3 | 70% or more | No void |

Referring to Table 3-2, the thin films formed of the hardmask compositions according to Examples 5 to 11 showed excellent planarization and no void and, thus, excellent gap-fill characteristics compared with the thin films formed of the hardmask compositions according to Comparative Examples 2 and 3.

Evaluation 4: Pattern Formation

A 3,000 Å-thick silicon oxide ($SiO_2$) layer was formed on a silicon wafer in a chemical vapor deposition (CVD) method. Subsequently, the hardmask compositions (monomer content: 13.0 weight based on the total composition)

according to Examples 5 to 11 and Comparative Examples 2 and 3 were respectively coated on the silicon oxide layer and heat-treated on a hot plate at 400° C. for 2 minutes to form each hardmask layer. Subsequently, a silicon nitride (SiN) layer was formed on the hardmask layer in a chemical vapor deposition (CVD) method. Subsequently, a photoresist for KrF was coated on the silicon nitride layer, heat-treated at 110° C. for 60 seconds, exposed using an ASML (XT: 1400, NA 0.93) exposure equipment, and developed with a 2.38 wt % tetramethylammonium hydroxide (TMAH) aqueous solution. Subsequently, the patterned photoresist was used as a mask, and the silicon nitride layer was dry etched using a mixed gas of $CHF_3/CF_4$. Subsequently, the patterned silicon nitride layer was used as a mask, the hardmask layer was dry etched with a mixed gas of $N_2/O_2$, the patterned hardmask layer was used as a mask, and a silicon oxide layer was dry etched by using a mixed gas of $CHF_3/CF_4$. Subsequently, an $O_2$ gas was used to remove an organic material remaining there.

An scanning electronic microscope (SEM) was used to examine the pattern cross section of the hardmask layer and the silicon oxide layer.

The results are provided in Table 4-1.

TABLE 4-1

|  | Hardmask layer pattern profile | Silicon oxide layer pattern profile |
| --- | --- | --- |
| Example 5 | vertical shape | vertical shape |
| Example 6 | vertical shape | vertical shape |
| Example 7 | vertical shape | vertical shape |
| Example 8 | vertical shape | vertical shape |
| Example 9 | vertical shape | vertical shape |
| Example 10 | vertical shape | vertical shape |
| Example 11 | vertical shape | vertical shape |
| Comparative Example 2 | tapered shape | tapered shape |
| Conipative Example 3 | tapered shape | tapered shape |

Referring to Table 4-1, the hardmask layers formed of the hardmask compositions according to Examples 5 to 11 and the silicon oxide layers beneath them were patterned into a vertical shape, while 4-1, the hardmask layers formed of the hardmask compositions according to according to Comparative Examples 2 and 3 were not patterned into a vertical shape but a tapered shape.

Accordingly, the hardmask layers using the hardmask compositions according to Examples 5 to 11 showed excellent etch resistance and, thus, were formed into a good pattern compared with the thin films using the hardmask compositions according to Comparative Examples 2 and 3, and, thus, the layers beneath the hardmask layers were also formed into a good pattern.

A 3,000 Å-thick silicon oxide $SiO_2$ layer was formed on a silicon wafer in a chemical vapor deposition ((VD) method. Subsequently, the hardmask compositions including a monomer of 13.0 wt % according to Examples 12 to 16 and Comparative Example 4 were respectively spin-on coated on the silicon oxide layer and heat-treated on a hot plate at 240° C. for 1 minute to form each hardmask layer. Subsequently, a silicon nitride (SiN) layer was respectively formed on the hardmask layers in a chemical vapor deposition (CVD) method. The pattern cross section of the hardmask layer and the silicon oxide layer were examined by treating the hardmask layer and the silicon oxide layer under the same other conditions as above.

The results are provided in Table 4-2.

TABLE 4-2

|  | Hardmask layer pattern profile | Silicon oxide layer pattern profile |
| --- | --- | --- |
| Example 12 | vertical shape | vertical shape |
| Example 13 | vertical shape | vertical shape |
| Example 14 | vertical shape | vertical shape |
| Example 15 | vertical shape | vertical shape |
| Example 16 | vertical shape | vertical shape |
| Comparative Example 4 | tapered shape | tapered shape |

Referring to Table 4-2, the hardmask layers formed of the hardmask compositions according to Examples 12 to 6 and the silicon oxide layer beneath the hardmask layers were all patterned into a vertical shape, while the hardmask layer formed of the hardmask composition according to Comparative Example 4 was patterned into a tapered shape.

Accordingly, the hardmask layers formed of the hardmask compositions according to Examples 12 to 6 showed excellent etch resistance and were formed into a good pattern compared with the hardmask layer formed of the hardmask composition according to Comparative Example 4, and, thus, the layers beneath the hardmask layers according to Examples 12 to 6 were also patterned into a good pattern.

Evaluation 5: Heat Resistance

The hardmask compositions (monomer content: 10.0 wt % based on the total composition) according to Examples 5 to 10 and Comparative Example 2 were respectively spin-on coated on a silicon wafer and heat-treated on a hot plate at 240° C. for 1 minute. A thin film thickness measurement device made by K-MAC was used to measure thickness of the thin films. Subsequently, the thin films were heat-treated at 400° C. for 2 minutes, and then thickness of the thin films was measured.

Outgassing during the heat treatment at 240° C. and 400° C. was examined with naked eyes.

The results are provided in Table 5-1.

TABLE 5-1

|  | Decrease ratio of thin film thickness (%) | Out-gassing |
| --- | --- | --- |
| Example 5 | −6.34 | None |
| Example 6 | −5.92 | None |
| Example 7 | −6.71 | None |
| Example 8 | −9.68 | None |
| Example 9 | −7.73 | None |
| Example 10 | −7.71 | None |
| Comparative Example 2 | −34.08 | Occurred when heat-treated at 400° C. |

Referring to Table 5-1, the thin films formed of the hardmask compositions according to Examples 5 to 10 showed a lower thickness decrease ratio than the thin films formed of the hardmask compositions according to Comparative Example 2 during the heat treatment at 400° C.

In addition, the thin films formed of the hardmask compositions according to Examples 5 to 10 showed no outgassing at 400° C. unlike the thin film formed of the hardmask composition according to Comparative Example 2.

Accordingly, without being bound by theory, it is believed that the thin films formed of the hardmask compositions according to Examples 5 to 10 had higher cross-linking and, thus, showed higher heat resistance at a high temperature of 400° C. than the thin film formed of the hardmask composition according to Comparative Example 2.

The hardmask compositions including a monomer of 10.0 wt % according to Examples 12 to 16 and Comparative Example 4 were respectively spin-on coated on a silicon wafer and heat-treated on a hot plate at 240° C. for 1 minute. A thin film thickness measurement device made by K-MAC was used to measure thickness of the thin films. Subsequently, thickness of the thin films was measured again after heat-treating the thin films at 400° C. for 2 minutes.

Outgassing was examined with naked eyes during the heat treatments at 240° C. and 400° C.

The results are provided in Table 5.

TABLE 5-2

|  | Thin film thickness after being heat-treated at 240° C. (Å) | Thin film thickness after being heat-treated at 400° C. (Å) | Decrease ratio of thin film thickness (%) | Outgassing |
|---|---|---|---|---|
| Example 12 | 2603 | 2160 | −17 | None |
| Example 13 | 2422 | 2248 | −7.2 | None |
| Example 14 | 2910 | 2829 | −2.8 | None |
| Example 15 | 2835 | 2566 | −9.5 | None |
| Example 16 | 2701 | 2606 | −3.5 | None |
| Comparative Example 4 | 2668 | 1841 | −31 | Occurred at 400° C. |

Referring to Table 5-2, the thin films formed of the hardmask compositions according to Examples 12 to 16 showed a lower thickness decrease ratio than the thin film formed of the hardmask composition according to Comparative Example 4.

In addition, the thin films formed of the hardmask compositions according to Examples 12 to 16 showed no outgassing at 400° C. unlike the thin film formed of the hardmask composition according to Comparative Example 4.

Accordingly, the thin films formed of the hardmask compositions according to Examples 12 to 16 had higher cross-linking and higher heat resistance at a high temperature of 400° C. than the thin film formed of the hardmask composition according to Comparative Example 4.

Evaluation 6: Optical Properties

The hardmask compositions (monomer content: 13.0 weight based on the total composition) according to Examples 5 to 10 and Comparative Example 2 were respectively spin-on coated on a silicon wafer having silicon nitride and baked at 400° C. for 120 seconds to form respective 800 Å-thick hardmask layers.

Refractive index (n) and extinction coefficient (k) of the hardmask layers were measured. The refractive index and extinction coefficient were measured by using an ellipsometer (J.A. Woollam Co.) while the thin film were radiated by light having a wavelength ranging from 193 nm to 633 nm.

The results are provided in Table 6.

TABLE 6

|  | Optical properties 193 nm | | Optical properties 633 nm | |
|---|---|---|---|---|
|  | Refractive index (n) | Extinction coefficient (k) | Refractive index (n) | Extinction coefficient (k) |
| Example 5 | 1.455 | 0.591 | 1.871 | 0.043 |
| Example 6 | 1.44 | 0.512 | 1.861 | 0.049 |
| Example 7 | 1.442 | 0.56 | 1.862 | 0.046 |
| Example 8 | 1.453 | 0.585 | 1.888 | 0.053 |
| Example 9 | 1.45 | 0.578 | 1.878 | 0.051 |
| Example 10 | 1.442 | 0.56 | 1.862 | 0.046 |
| Comparative Example 2 | 1.295 | 0.525 | 1.946 | 0.108 |

Referring to Table 6, the resist underlayer compositions according to Examples 5 to 10 showed a refractive index and an extinction coefficient usable as an anti-reflection coating layer in wavelengths of ArF (193 nm) and KrF (248 nm).

Evaluation 7: Chemical Resistance

The hardmask compositions including a monomer of 10.0 wt % according to Examples 12 to 16 and Comparative Example 4 were spin-on coated on a silicon wafer and heat-treated on a hot plate at 240° C. for 1 minute to form each thin film. A thin film thickness measurement device made by K-MAC was used to measure thickness of the thin films.

Subsequently, the thin films were dipped in a mixed solvent of ethyl 3-ethoxypropionate (EEP) and ethyl lactate (EL) (7:3 (v/v)) as a stripper for one minute, and then thickness of the thin films was measured.

The results are provided in Table 7.

TABLE 7

|  | Initial thin film thickness (Å) | Thin film thickness after dipping (Å) | Decrease ratio of thin film thickness (%) |
|---|---|---|---|
| Example 12 | 2553 | 1736 | −32 |
| Example 13 | 2475 | 2247 | −9.2 |
| Example 14 | 2995 | 2988 | −0.23 |
| Example 15 | 2821 | 2660 | −5.7 |
| Example 16 | 2662 | 2657 | −0.19 |
| Comparative Example 4 | 2680 | 375 | −86 |

Referring to Table 7, the thin films formed of the hardmask compositions according to Examples 12 to 16 showed a lower thickness decrease ratio after the dipping than the thin film formed of the hardmask composition according to Comparative Example 4.

Accordingly, without being bound by theory, it is believed that the hardmask compositions according to Examples 12 to 16 had sufficient cross-linking during the heat treatment at a relatively low temperature of 240° C. and showed higher chemical resistance relative to the hardmask composition according to Comparative Example 4.

By way of summation and review, a typical lithographic technique includes providing a material layer on a semiconductor substrate; coating a photoresist layer thereon; exposing and developing the same to provide a photoresist pattern; and etching the material layer using the photoresist pattern as a mask. A hardmask layer may be formed between the material layer and the photoresist layer to provide a fine pattern. The hardmask layer plays a role of an intermediate layer for transferring the fine pattern of photoresist to the material layer through a selective etching process. A hardmask layer that provides characteristics such as heat resistance and etch resistance may better tolerate multiple etching processes. A hardmask layer may be formed by a spin-on coating method instead of, e.g., chemical vapor deposition. The spin-on coating method is easy to perform, and may also improve gap-fill characteristics and planarization characteristics. The spin-on coating method may use a hardmask composition having solubility in a solvent, but the above characteristics desired in a hardmask layer may have a negative effect on solubility.

As described above, embodiments may provide a hardmask composition that provides heat resistance and etch resistance while providing solubility in a solvent, gap-fill characteristics, and planarization characteristics. Characteristics such as heat resistance, etch resistance, planarization characteristics, and gap-fill characteristics may be improved for the hardmask layer.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A monomer for a hardmask composition, wherein the monomer is represented by Chemical Formula 1a, 1c to 1k, or 1n to 1o:

[Chemical Formula 1a]

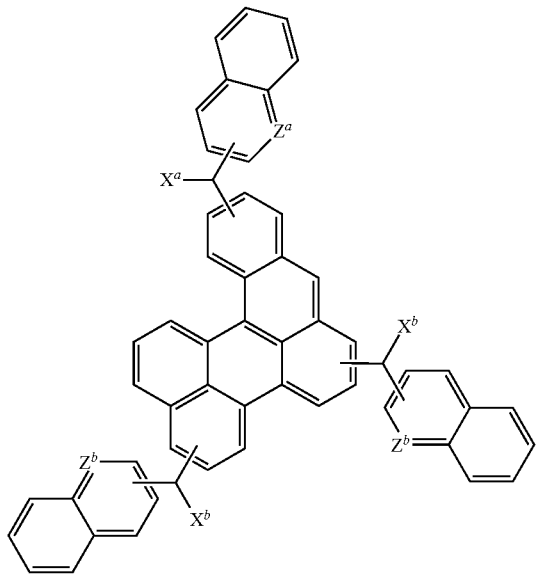

[Chemical Formula 1c]

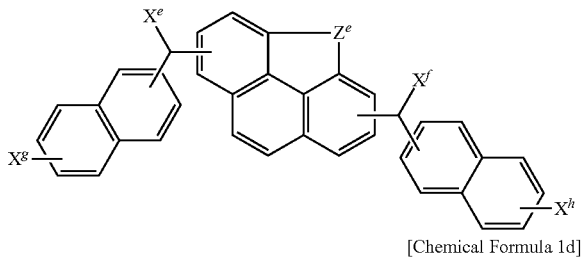

[Chemical Formula 1d]

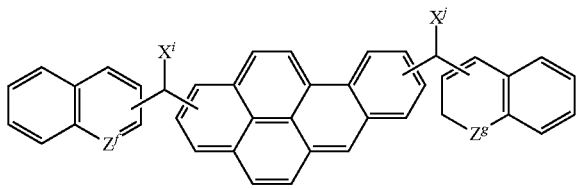

wherein, in the above Chemical Formulae 1a, 1c, and 1d,
$X^a$, $X^b$, $X^e$, $X^f$, $X^g$, $X^h$, $X^i$ and $X^j$ are independently a hydroxy group, a halogen atom, a halogen-containing group, a thionyl group, a thiol group, a cyano group, a substituted or unsubstituted amino group, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C30 alkoxy group, a substituted or unsubstituted C2 to C30 alkenyl group, a substituted or unsubstituted C2 to C30 alkynyl group, a substituted or unsubstituted C1 to C20 aldehyde group, a substituted or unsubstituted C1 to C4 alkyl ether, a substituted or unsubstituted C7 to C20 arylalkylene ether, a substituted or unsubstituted C1 to C30 haloalkyl group, a substituted or unsubstituted C1 to C20 alkylborane group, a substituted or unsubstituted C6 to C30 arylborane group, or a combination thereof, $Z^e$ is a single bond, a substituted or unsubstituted C1 or C3 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, $Z^g$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, $Z^a$, $Z^b$, and $Z^f$ are independently nitrogen (N), CR, or a combination thereof, and R is hydrogen, a substituted or unsubstituted C1 to C10 alkyl group, a halogen atom, a halogen-containing group, or a combination thereof,

[Chemical Formula 1e]

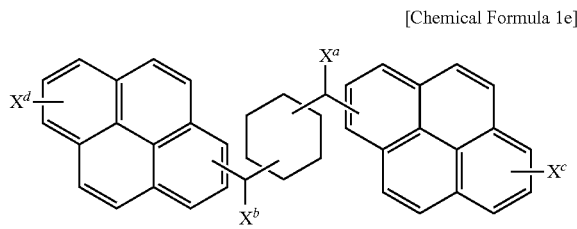

[Chemical Formula 1f]

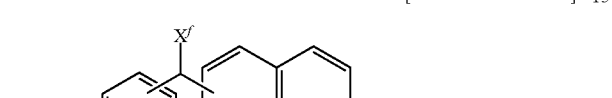

[Chemical Formula 1g]

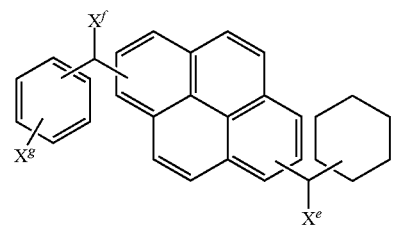

[Chemical Formula 1h]

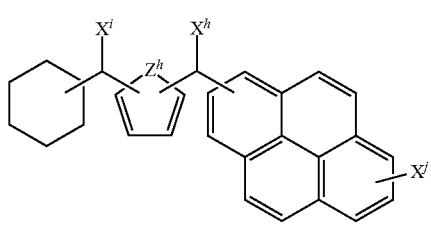

[Chemical Formula 1i]

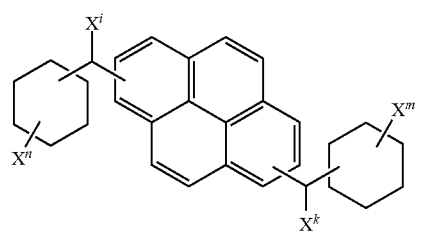

[Chemical Formula 1j]

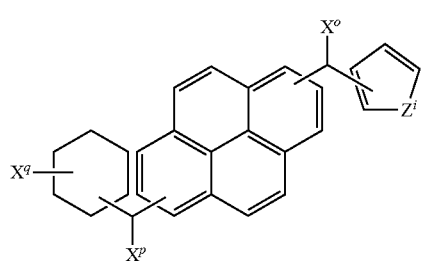

[Chemical Formula 1k]

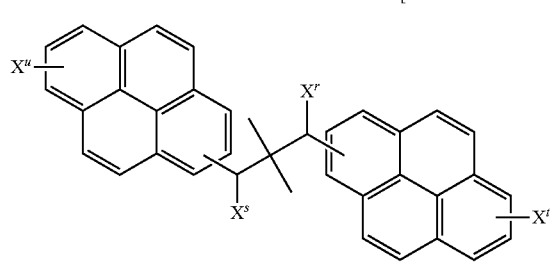

wherein, in the above Chemical Formulae 1 e to 1k, $X^a$ to $X^y$ are each independently a hydroxy group, a thionyl group, a thiol group, a cyano group, a substituted or unsubstituted amino group, a halogen atom, a halogen-containing group, a substituted or unsubstituted C1 to C30 alkoxy group, or a combination thereof, and $Z^h$ and $Z^i$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof:

[Chemical Formula 1n]

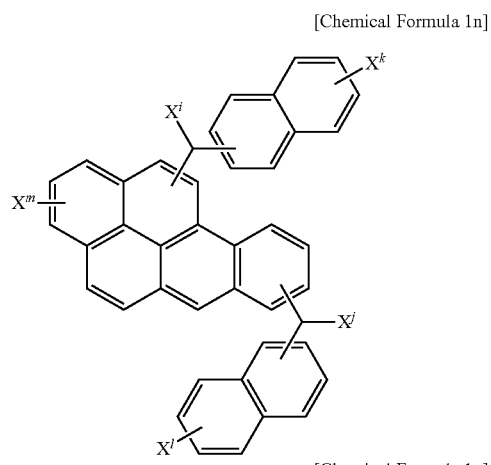

[Chemical Formula 1o]

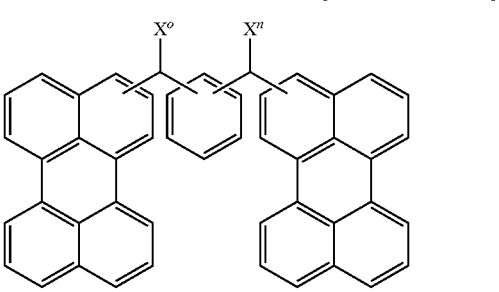

wherein, in the above Chemical Formulae 1n and 1o, $X^i$ to $X^o$ are each independently a hydroxy group, a halogen atom, a halogen-containing group, a thionyl group, a thiol group, a cyano group, a substituted or unsubstituted amino group, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C30 alkoxy group, a substituted or unsubstituted C2 to C30 alkenyl group, a substituted or unsubstituted C2 to C30 alkynyl group, a substituted or unsubstituted C1 to C20 aldehyde group, a substituted or unsubstituted C1 to C4 alkyl ether, a substituted or unsubstituted C7 to C20 arylalkylene ether, a substituted or unsubstituted C1 to C30 haloalkyl group, a substituted or unsubstituted C1 to C20 alkylborane group, a substituted or unsubstituted C6 to C30 arylborane group, or a combination thereof.

2. The monomer for a hardmask composition as claimed in claim 1, wherein the monomer has a molecular weight of about 200 to about 5,000.

3. A hardmask composition, comprising:
the monomer as claimed in claim 1; and
a solvent.

4. The hardmask composition as claimed in claim 3, wherein the monomer has a molecular weight of about 200 to about 5,000.

5. The hardmask composition as claimed in claim 3, wherein the monomer is included in an amount of about 0.1 to about 50 wt % based on the total amount of the hardmask composition.

6. A method of forming a pattern, the method comprising:
providing a material layer on a substrate,
applying the hardmask composition of claim 3 on the material layer,
heat-treating the hardmask composition to form a hardmask layer,
forming a silicon-containing thin layer on the hardmask layer,
forming a photoresist layer on the silicon-containing thin layer,
exposing and developing the photoresist layer to form a photoresist pattern, and
selectively removing the silicon-containing thin layer and the hardmask layer using the photoresist pattern to expose a part of the material layer, and
etching an exposed part of the material layer.

7. The method as claimed in claim 6, wherein the hardmask composition is applied using a spin-on coating method.

8. The method as claimed in claim 6, wherein forming the hardmask layer includes heat-treating at about 100° C. to about 500° C.

9. The method as claimed in claim 6, further comprising forming a bottom antireflective coating (BARC) on the silicon-containing thin layer.

10. The method as claimed in claim 9, wherein the silicon-containing thin layer includes silicon oxynitride (SiON).

* * * * *